United States Patent [19]

Cragoe, Jr. et al.

[11] 4,081,554
[45] Mar. 28, 1978

[54] 1-OXO-2,2-DISUBSTITUTED-5-INDANYLOXY(OR THIO)ALKANO ACIDS

[75] Inventors: Edward J. Cragoe, Jr., Lansdale; Otto W. Woltersdorf, Jr., Chalfont, both of Pa.

[73] Assignee: Merck & Co., Inc., Rahway, N.J.

[21] Appl. No.: 704,853

[22] Filed: Jul. 13, 1976

Related U.S. Application Data

[62] Division of Ser. No. 399,571, Sep. 21, 1973, Pat. No. 3,984,465.

[30] Foreign Application Priority Data

Oct. 13, 1972 Canada ................................. 153821
Aug. 28, 1973 Canada ................................. 178824

[51] Int. Cl.$^2$ ...................... A61K 31/19; C07C 69/76; A61K 31/235; A61K 31/165

[52] U.S. Cl. ...................................... 424/317; 560/10; 560/53; 260/308 D; 260/473 F; 260/520 C; 260/558 S; 260/559 B; 424/250; 424/262; 424/269; 424/308; 424/319; 424/324

[58] Field of Search ...................... 424/308, 317, 324; 260/520 C, 473 F, 558 S, 559 B

[56] References Cited

U.S. PATENT DOCUMENTS 3,668,241  6/1972  Cragoe et al. ................... 424/315 X Primary Examiner—Frederick E. Waddell
Attorney, Agent, or Firm—Michael C. Sudol, Jr.

[57] ABSTRACT

1-Oxo-2,2-disubstituted-5-indanyloxy(or thio)alkanoic acids and their salt, ester, anhydride, amide and 5-tetrazolyl derivatives are disclosed. The products display a dual pharmaceutical utility in that they exhibit diuretic, saluretic and uricosuric activity. The acid products are prepared by treating a 2,2-disubstituted-5-hydroxy(or mercapto)-1-indanone with an haloalkanoic acid or ester thereof and, if the ester is employed, hydrolyzing the ester.

13 Claims, No Drawings

1-OXO-2,2-DISUBSTITUTED-5-INDANYLOXY(OR THIO)ALKANO ACIDS

This case is a divisional of U.S. Ser. No. 399,571 filed Sept. 21, 1973 now U.S. Pat. No. 3,984,465 which issued on Oct. 5, 1976.

This invention relates to a new class of chemical compounds which can be described generally as 1-oxo-2,2-disubstituted-5-indanyloxy(or thio)alkanoic acids and to the non-toxic, pharmacologically acceptable salt, ester, anhydride, amide and 5-tetrazolyl derivatives. It is also an object of this invention to describe a method for the preparation of the 1-oxo-2,2-disubstituted-5-indanyloxyalkanoic acids. Pharmacological studies show that the instant products are effective diuretic and saluretic agents which can be used in the treatment of conditions associated with electrolyte and fluid retention. The instant products are also useful in the treatment of hypertension. In addition, these compounds are able to maintain the uric acid concentration in the body at pretreatment levels or to even effect a decrease in the uric acid concentration. All of the compounds of this invention possess the described utilities; however, by structural modifications various ratios of these activities are observed.

When administered in therapeutic dosages, in conventional vehicles, the instant products effectively reduce the amount of sodium and chloride ions in the body, lower dangerous excesses of fluid levels to acceptable levels and, in general, alleviate conditions usually associated with edema. In addition, these compounds overcome a major problem associated with many of the presently available diuretics and saluretics. Many of the presently available diuretics and saluretics have a tendency upon administration to induce hyperuricemia which may precipitate uric acid or sodium urate, or both, in the body which may cause from mild to severe cases of gout. The instant compounds of this invention now provide an effective tool to treat those patients (both human and animal) requiring diuretic and saluretic treatment without incurring the risk of inducing gout.

The 1-oxo-2,2-disubstituted-5-indanyloxy(or thio)-alkanoic acids (I) of the invention have the following structural formula:

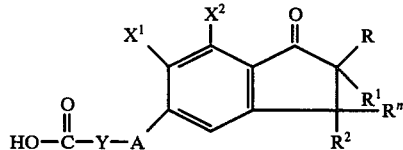

wherein A is oxygen or sulfur; R is lower alkyl containing from 1 to 5 carbon atoms such as methyl, ethyl, n-propyl isopropyl, n-butyl, isobutyl, tert-butyl, n-pentyl and the like; cycloalkyl, for example, cycloalkyl containing from 3–6 nuclear carbon atoms such as cyclopropyl, cyclobutyl, cyclopentyl, cyclohexyl and the like; $R^1$ is lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl and the like, halo lower alkenyl containing from 3 to 5 carbon atoms such as 2-chloroallyl, 2-chloro-2-butenyl, 2-chloro-2-pentenyl and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl, phenylpropyl and the like, phenyl lower alkenyl such as cinnamyl and the like, hydroxy lower alkyl, for example, hydroxymethyl and the like, hydroxycycloalkyl, for example, hydroxycyclopentyl or hydroxycyclohexyl, cycloalkylalkyl containing 4 to 7 carbon atoms, for example, cyclopropylmethyl, cyclopentylmethyl and the like, lower alkoxyloweralkyl, oxolower alkyl and the like or R and $R^1$ may be joined together with the carbon atoms to which they are attached to form a cycloalkyl radical containing from 3 to 7 nuclear carbon atoms which may be unsubstituted or lower alkyl or hydroxy substituted, for example, cyclopropyl, cyclobutyl, cyclopentyl, cyclohexyl, cycloheptyl, methylcyclopropyl, hydroxycyclopentyl, and the like; $R^2$ is hydrogen, halo, for example, chloro, bromo and the like, lower alkyl containing from 1 to 5 carbon atoms, aryl such as phenyl or substituted aryl wherein the substituent is lower alkyl or halo; $R^n$ is hydrogen or methyl; $X^1$ is hydrogen, methyl or halo such as chloro, bromo, fluoro and the like and $X^2$ is methyl or halo such as chloro, bromo, fluoro and the like or $X^1$ and $X^2$ may be joined to form a hydrocarbylene chain containing from 3 to 4 carbon atoms, for example, trimethylene, tetramethylene, 1,3-butadienylene and the like, and Y is an alkylene or haloalkylene radical having a maximum of 4 carbon atoms which contain from 1–3 linear carbon atoms between the oxy (or thio) and carboxy group, for example, methylene, ethylidene, propylidene, isopropylidene, ethylene, trimethylene, fluoromethylene and the like. The invention also includes the pharmaceutically acceptable salts, the ester, anhydride and amide derivatives and the derivatives wherein a 5-tetrazolyl radical replaces the carboxy group.

A preferred aspect of this invention are compounds of Formula I above wherein A is oxygen, Y is —$CH_2$—, $X^1$, $X^2$, R, $R^1$, $R^2$ and $R^n$ are as above defined and the nontoxic pharmaceutically acceptable salts thereof.

More preferred embodiments of this invention are the (1-oxo-2,2-disubstituted-6,7-disubstituted-5-indanyloxy)-acetic acids having the following structural formula:

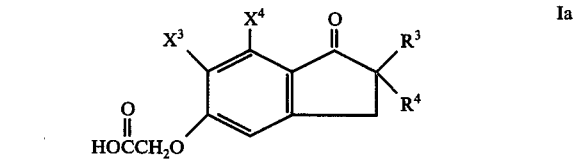

wherein $R^3$ is lower alkyl containing from 1 to 3 carbon atoms such as methy, ethyl, n-propyl or isopropyl or cycloalkyl containing 5 or 6 nuclear carbon atoms such as cyclopentyl or cyclohexyl, hydroxycycloalkyl containing 4 to 6 carbon atoms such as hydroxycyclopentyl or hydroxycyclohexyl, or phenyl loweralkyl such as benzyl and $R^4$ is lower alkyl containing from 1 to 3 carbon atoms such as methyl, ethyl, n-propyl or isopropyl; or $R^3$ and $R^4$ may be joined together with the carbon atom to which they are attached to form a cycloalkyl radical containing from 5 to 6 nuclear carbon atoms such as cyclopentyl, cyclohexyl and the like, and $X^3$ and $X^4$ are the same or different radicals selected from methyl or chloro and the non-toxic, pharmacologically acceptable salt derivatives. The foregoing class of compounds exhibits particularly good diuretic and saluretic activity and also either maintains the uric acid concentration in the body at pretreatment levels or even causes a decrease in the uric acid concentration.

The 1-oxo-2,2-disubstituted-5-indanyloxy(or thio)-alkanoic acids and ester (I) wherein Y contains 1 or 3 linear carbon atoms may be prepared by an etherification method which comprises reacting a haloacetic acid or ester thereof of the formula:

wherein $R^5$ is hydrogen or lower alkyl such as methyl, ethyl and the like and Z is halo such as bromo, chloro, iodo and the like with a suitable 2,2-disubstituted-5-hydroxy(or mercapto)-1-indan-one (II, infra). The following equation illustrates this reaction:

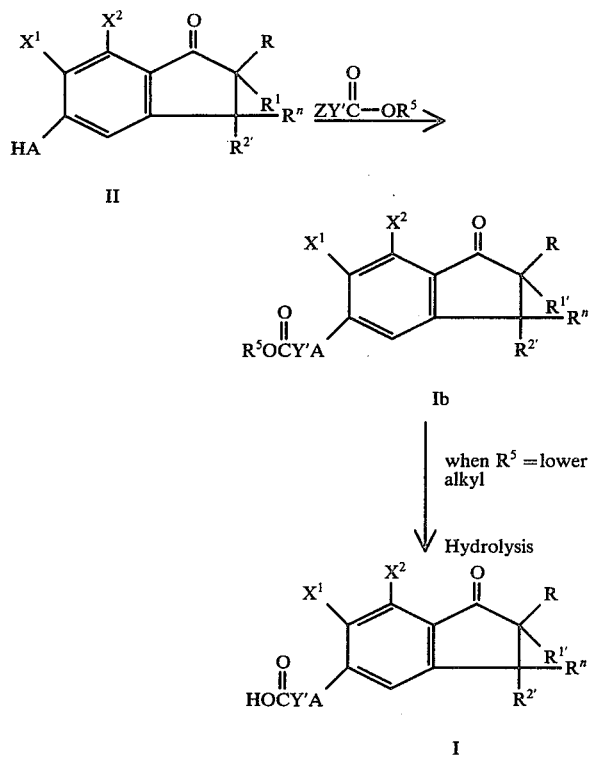

wherein $X^1$, $X^2$, R, $R^5$ and Z are as defined above; $R^{1'}$ is lower alkyl, lower alkenyl, halo lower alkenyl, lower alkynyl, phenyl lower alkyl, cycloalkyl alkyl containing 4 to 7 carbon atoms, loweralkoxy lower alkyl, oxoloweralkyl or phenyl lower alkenyl, wherein these substituents are as defined above under the definition of $R^1$; or R and $R^{1'}$ may be joined together with the carbon atom to which they are attached to form a cycloalkyl radical containing from 4 to 7 nuclear carbon atoms; Y is an alkylene or haloalkylene radical containing 1 or 3 linear carbon atoms as defined above, $R^{2'}$ is hydrogen or lower alkyl aryl or substituted aryl and $R^n$ is hydrogen or methyl. In general, the reaction is conducted in the presence of a base such as an alkali metal carbonate, hydroxide or alkoxide such as potassium carbonate, sodium carbonate, potassium hydroxide, sodium hydroxide, sodium ethoxide and the like. Any solvent which is inert or substantially inert to the reactants and in which the reagents are reasonably soluble may be employed. Acetone, ethanol and dimethylformamide, for example, have proved to be particularly advantageous solvents. The reaction may be conducted at a temperature in the range of from about 25° C. to the reflux temperature of the particular solvent employed. The reaction with the haloacetic acid or ester is generally complete in about 10 to 60 minutes. If the haloacetic acid ester is employed, the ester obtained may be hydrolyzed to the free acid by methods well known to those skilled in the art.

Another novel process of this invention consists in pyrolyzing a tert-butyl (1-oxo-2,2-disubstituted indanyloxy)acetate of the formula:

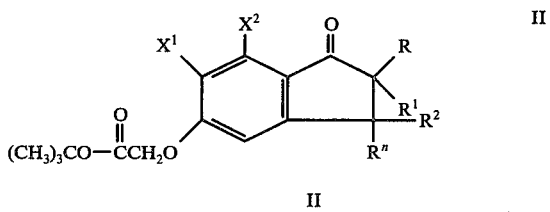

wherein R is lower alkyl containing from 1 to 5 carbon atoms such as methyl, ethyl, n-propyl, isopropyl, n-butyl, isobutyl, tert-butyl, n-pentyl and the like; cycloalkyl, for example, cycloalkyl containing from 3–6 nuclear carbon atoms such as cyclopentyl, cyclohexyl and the like; $R^1$ is lower alkyl containing from 1 to 5 carbon atoms such as methyl, ethyl, n-propyl, isopropyl, n-butyl, isobutyl, tert-butyl, n-pentyl and the like, lower alkenyl containing from 3 to 5 carbon atoms such as allyl, 1-, 2- or 3-butenyl, 1-, 2-, 3- or 4-pentenyl and the like, halo lower alkenyl containing from 3 to 5 carbon atoms such as 2 chloroallyl, 2-chloro-2-butenyl, 2-chloro-2-pentenyl and the like, lower alkynyl containing from 3 to 5 carbon atoms such as propargyl, 1-, 2- or 3-butynyl, 1-, 2-, 3- or 4-pentynyl and the like, phenyl lower alkyl wherein the lower alkyl contains from 1 to 3 carbon atoms such as benzyl, phenethyl, phenylpropyl and the like, phenyl lower alkenyl such as cinnamyl and the like, hydroxycycloalkyl, for example, hydroxycyclopentyl or hydroxycyclohexyl and the like, cycloalkyl alkyl containing 4–7 carbon atoms for example cyclopropylmethyl, cyclopentylmethyl and the like, loweralkoxy lower alkyl or oxolower alkyl, or R and $R^1$ may be joined together with the carbon atoms to which they are attached to form a cycloalkyl radical containing from 3 to 7 nuclear carbon atoms which may be unsubstituted hydroxy or lower alkyl substituted, for example, cyclopropyl, cyclobutyl, cyclopentyl, cyclohexyl, cycloheptyl, methylcyclopropyl, hydroxycyclopentyl and the like; $R^2$ is hydrogen, halo, for example, chloro, bromo and the like or lower alkyl containing from 1 to 5 carbon atoms or aryl such as phenyl or substituted aryl wherein the substituent is lower alkyl or halo; $R^n$ is hydrogen or methyl; $X^1$ is hydrogen, methyl or halo such as chloro, bromo, fluoro and the like and $X^2$ is methyl or halo such as chloro, bromo, fluoro and the like or $X^1$ and $X^2$ may be joined to form a hydrocarbylene chain containing from 3 to 4 carbon atoms, for example, trimethylene, tetramethylene, 1,3-butadienylene and the like, by heating the ester in the presence of a strong acid, for example, in the presence of p-toluenesulfonic acid, sulfuric acid, benzenesulfonic acid, gaseous hydrogen chloride, and the like. In general, pyrolysis is effected by heating at a temperature in the range of from about 70°–140° C. and, preferably, in the range of from about 80°–100° C. Also, the reaction may be conducted without a solvent or in the presence of a suitable non-aqueous medium in which the reactants are reasonably soluble, for example in the presence of benzene, toluene, xylene, and the like.

Those 1-oxo-2,2-disubstituted-5-indanyloxy(or thio)alkanoic acids (I) wherein the alkylene chain contains 2 linear carbon atoms between the carboxy and oxy (or thio) groups are prepared from their corresponding 2,2-disubstituted-5-hydroxy(or mercapto)-1-indanones (II) by the reaction of the latter with propiolactone or with an appropriately substituted propiolactone, in the presence of a base such as an aqueous solution of sodium hydroxide, preferably, while heating the solution at reflux temperatures; followed by the acidification of the carboxylate intermediate thus formed to the desired acid. The following equation illustrates the reaction:

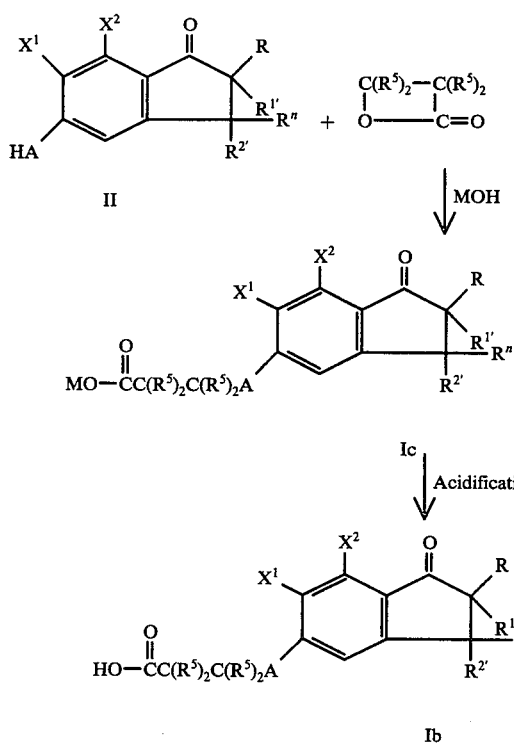

wherein A, R, $R^{1'}$, $R^{2'}$, $R^n$, $R^5$, $X^1$ and $X^2$ are as defined above and M is a cation derived from an alkali metal hydroxide or alkali metal carbonate such as a sodium or potassium cation.

The 2,2-disubstituted-5-hydroxy-(or mercapto)-1-indanones (II, infra), which also exhibit diuretic and uricosuric activity, are prepared by treating the correspondingly substituted 2,2-disubstituted-5-lower alkoxy(or lower alkylthio)-1-indanone with an ether cleaving reagent such as aluminum chloride, pyridine hydrochloride, sodium in liquid ammonia and the like. When aluminum chloride is employed, the solvent may be heptane, carbon disulfide, methylene chloride and the like and when pyridine hydrochloride is employed, it is not necessary to employ a solvent. The following equation illustrates this process:

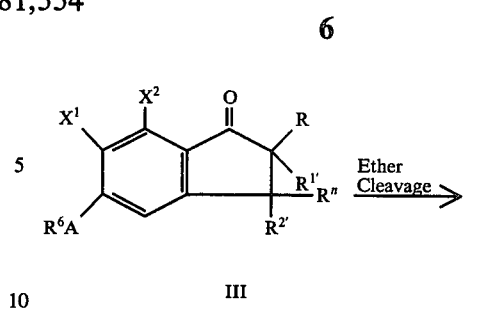

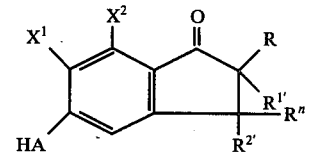

wherein A, R, $R^{1'}$, $R^{2'}$, $R^n$, $X^1$ and $X^2$ are as defined above, and $R^6$ is lower alkyl.

The 2,2-disubstituted-5-lower-alkoxy-(or lower alkyl thio)-1-indanones (III, supra) which exhibit uricosuric activity are prepared by treating a 2-substituted-5-lower alkoxy (or lower alkyl thio)-1-indanone (IV, infra) with a suitable alkylating reagent of the formula: $R^{1'}Z$ wherein $R^{1'}$ and Z are as defined above. This reaction is conducted by first treating the 2-substituted-5-lower alkoxy-1-indanone (IV) with a suitable base, for example, an alkali metal hydride such as sodium hydride and the like, or an alkali metal alkoxide, for example, potassium tertiary butoxide and the like. Other bases which may be employed include sodium amide, lithium amide and the like. This basified compound is then treated with the alkylating reagent, $R^{1'}Z$. Any solvent which is inert or substantially inert to the reactants employed may be used. Suitable solvents include, for example, 1,2-dimethoxyethane, tertiary butanol, benzene, dimethylformamide and the like. The reaction may be conducted at a temperature in the range of from about 25° to about 150° C. In general, the reaction is conducted at a temperature in the range of from about 75° to about 90° C. The following equation illustrates this process:

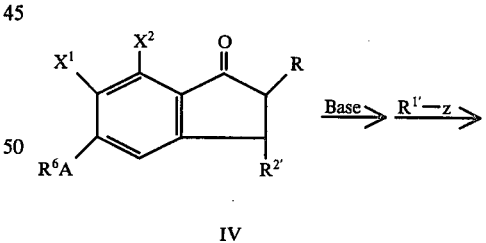

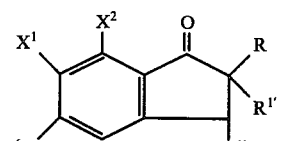

wherein A, R, $R^{1'}$, $R^{2'}$, $R^6$, $X^1$, $X^2$ and Z are as defined above.

The 2-substituted-5-lower alkoxy (and lower alkyl thio)-1-indanones (IV, supra) employed above may be prepared by several routes. One route comprises treating the 2-substituted-5-hydroxy-1-indanone with an alkylating agent such as dimethylsulfate or diethylsulfate in the presence of a base such as sodium hydroxide or potassium hydroxide. Other alkylating agents which may be employed include methyl iodide, ethyl iodide and the like employing dimethylformamide as the preferred solvent and as the base, potassium carbonate. The 2-substituted-5-hydroxy-(and 5-mercapto)-1-indanones employed in this particular procedure are known compounds described in U.S. Pat. No. 3,668,241.

A second method for preparing the 2-substituted-5-lower alkoxy-(and lower alkyl thio)-1-indanones (IV) comprises the cyclialkylation of a nuclear lower alkoxy (or lower alkyl thio) substituted (2-alkylidenealkanoyl)-benzene (V, infra) by treatment with an electron-acceptor acid, for example, a Lewis acid such as concentrated sulfuric acid, polyphosphoric acid, boron trifluoride and the like. The reaction may be conducted at a temperature in the range of from about 0° to about 60° C., in general, the reaction is conducted at ambient temperature. The following equation illustrates this process:

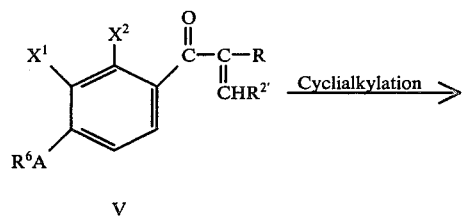

V

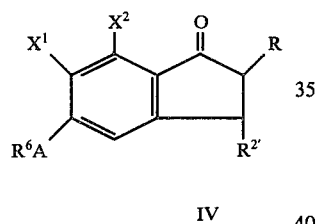

IV wherein A, R, $R^{2'}$, $R^6$, $X^1$ and $X^2$ are as defined above.

The 2-spiro-5-lower alkoxy-(and lower alkyl thio)-1-indanones (IVa) are prepared by treating a 2-(ω-haloalkyl)-5-lower alkoxy-(or lower alkylthio)-1-indanone (IVb) with a base, for example, an alkali metal hydride such as sodium hydride and the like in a suitable inert solvent such as 1,2-dimethoxyethane at the reflux temperature of the particular solvent employed. The following equation illustrates this process:

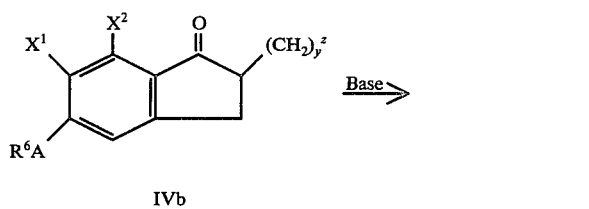

IVb

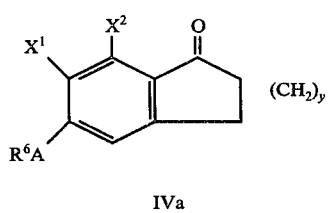

IVa wherein A, $R^6$, $X^1$, $X^2$ and Z are as defined above and y is an integer having a value of from 3 to 6.

The nuclear lower alkoxy (and lower alkyl thio) (2-alkylidenealkanoyl)benzenes (V, supra) employed above may be prepared by one of three methods. One method, limited to the preparation of the nuclear lower alkoxy-(or lower alkyl thio)-4-(2-methylenealkanoyl)-benzenes (Va), comprises treating a nuclear lower alkoxy-(or lower alkyl thio)-4-alkanoylbenzene (VI) with dimethylamine hydrochloride and paraformaldehyde followed by treatment of the Mannich intermediate (VIa), thus obtained, with aqueous sodium bicarbonate or anhydrous dimethylformamide, either with or without heat to afford the desired compound, Va. The following equation illustrates this process:

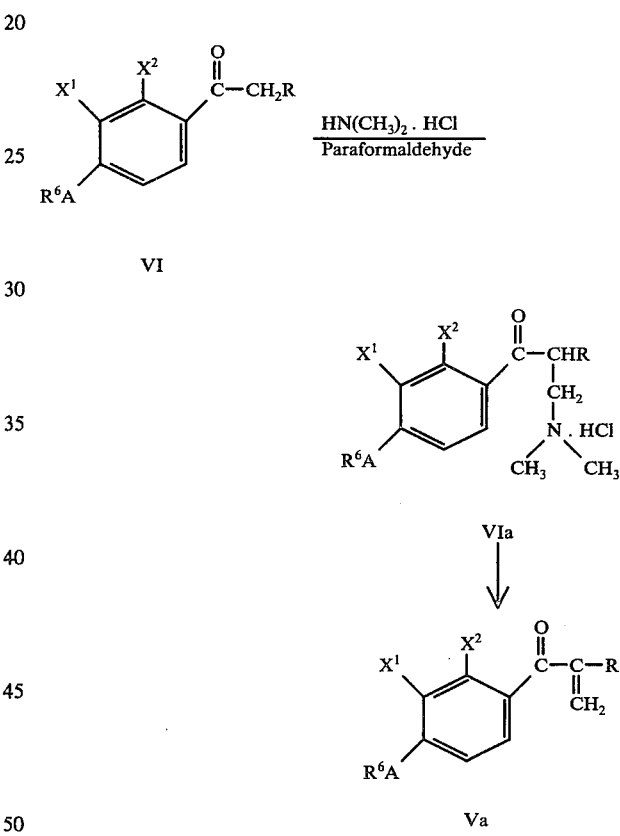

wherein A, R, $R^6$, $X^1$ and $X^2$ are as defined above.

A second method for preparing the nuclear lower alkoxy-(and lower alkyl thio)-2-(alkylidenealkanoyl)-benzenes (Vb) and one limited to preparing those compounds wherein R is methyl, comprises treating a nuclear lower alkoxy-(or lower alkyl thio) substituted 2-bromo-2-methylpropionylbenzene (VII, infra) with a dehydrobrominating agent such as lithium bromide, lithium chloride and the like. Suitable solvents for this reaction include dimethylformamide and the like. This reaction is conveniently conducted at a temperature in the range of from about 50° to about 120° C. for a period of time of from about 1 hour to about 6 hours. The following equation illustrates this reaction:

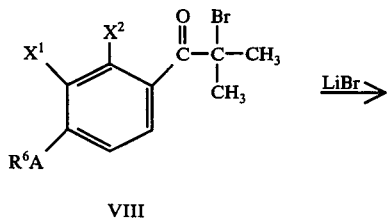

VIII

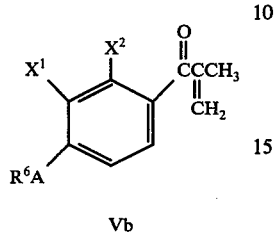

Vb wherein A, $R^6$, $X^1$ and $X^2$ are as defined above.

A third method for preparing the compounds of formula V and one limited to the preparation of the homologous 4-(2-alkylidenealkanoyl)benzenes (Vc), for example, the 4-(2-ethylidene) and 4-(2-propylidene) homologs, comprises treating a nuclear lower alkoxy (or lower alkylthio) substituted benzene (IX, infra) with an appropriate branched chain alkanoyl halide such as 2-methylbutyryl chloride, 2-ethylbutyryl chloride and the like in the presence of a Friedel-Crafts catalyst to afford the corresponding [4-nuclear lower alkoxy (or lower alkyl thio) substituted] alkanoylbenzene (VIIIa); which is halogenated and then dehydrohalogenated to afford the 4-(2-alkylidenealkanoyl)-benzene (Vc). The following equation illustrates this process:

the desired compound Vd. The following equation illustrates this process:

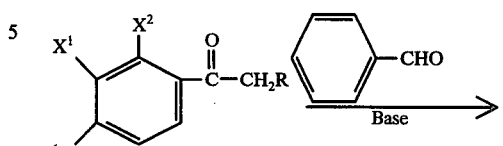

VIII

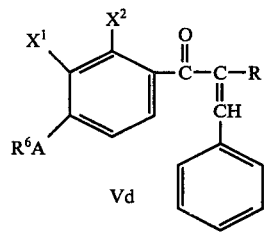

Vd wherein A, R, $R^6$, $X^1$ and $X^2$ are as defined above.

The [4-nuclear lower alkoxy (and lower alkyl thio) substituted]alkanoyl benzenes (VIII) are either known compounds or may be prepared by the reaction of an alkanoyl halide with a nuclear lower alkoxy (or lower alkyl thio) substituted benzene (IX, infra) in the presence of a Friedel-Crafts catalyst such as aluminum chloride and the like. The reaction solvent and the temperature at which the reaction is conducted are not particularly critical aspects of this reaction inasmuch as any solvent which is inert to the acyl halide and nuclear lower alkoxy (or lower alkyl thio) substituted benzenes may be employed with good results. In this regard, it

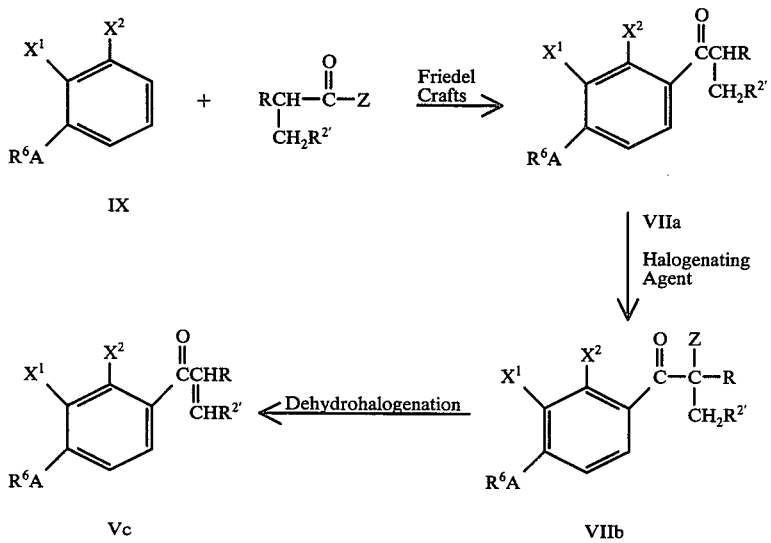

wherein A, R, $R^{2'}$, $R^6$, $X^1$, $X^2$ and Z are as defined above.

A fourth method for preparing compounds of Formula V, and one limited to the preparation of those compounds wherein $R^2$ in Formula I is phenyl, comprises treating a nuclear lower alkoxy(or alkylthio)-4-alkanoyl benzene (VIII) with benzaldehyde in a suitable solvent such as water, dimethylsulfoxide and the like in the presence of a base such as sodium hydroxide, potassium hydroxide, either with or without heat, to afford has been found that methylene chloride is a particularly suitable solvent. The following equation illustrates this reaction:

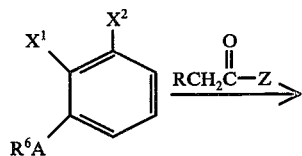

IX

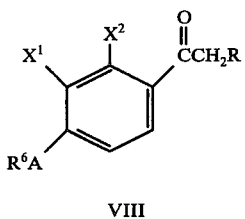

VIII wherein A, R, $R^6$, $X^1$, $X^2$ and Z are as defined above.

The nuclear lower alkoxy (and lower alkyl thio) substituted (2-bromo-2-methylpropionyl)benzenes employed above are prepared by the bromination of the correspondingly nuclear lower alkoxy (or lower alkyl thio) substituted (2-methylpropionyl)benzene employing standard brominating conditions. The following equation illustrates this process:

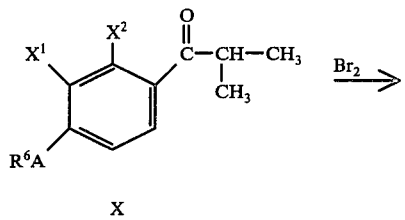

X

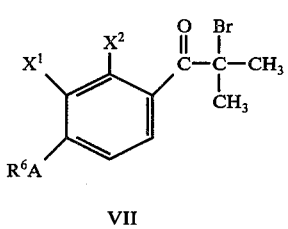

VII wherein A, $R^6$, $X^1$ and $X^2$ are as defined above.

The nuclear lower alkoxy (and lower alkyl thio) substituted (2-methylpropionyl)benzene (X) employed above are prepared in a similar manner as described above employing an isobutyryl halide in place of the alkanoyl halide described above. The following equation illustrates this reaction:

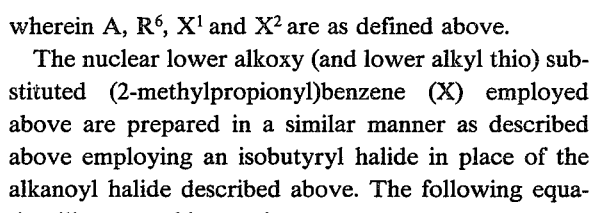

XI

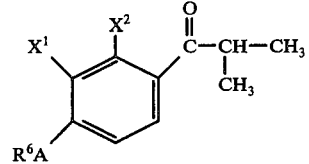

X wherein A, $R^6$, $X^1$, $X^2$ and Z are as defined above.

Those indanyloxyalkanoic acids wherein R and $R^1$ are joined to form a cyclopropyl or lower alkyl cyclopropyl may be prepared by treating the correspondingly substituted 2-alkylideneindanyloxyalkanoic acids with an alkali metal base such as sodium hydride and the like followed by treatment with a methylating agent, for example, trimethylsulfoxonium iodide and the like. The preparation of the 1-oxo-2-alkylideneindanyloxyalkanoic acids is described in Great Britain Pat. No. 1,254,908. The following equation illustrates this reaction:

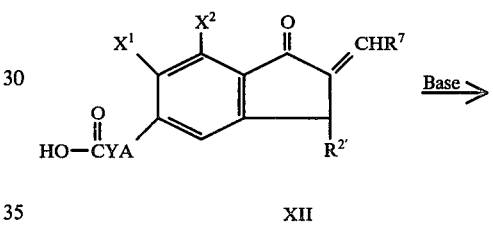

XII

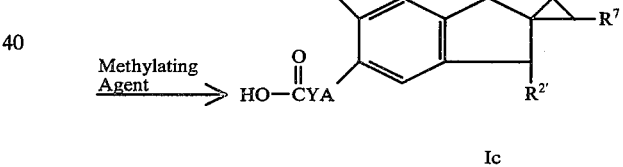

Ic wherein A, $R^{2'}$, $X^1$, $X^2$ and Y are as defined above and $R^7$ is hydrogen or lower alkyl of from 1 to 4 carbon atoms.

The 1-oxo-2,2-disubstituted-5-indanyloxyalkanoic acids, wherein $R^1$ is hydroxyloweralkyl, are prepared by treating a 1-oxo-2-substituted-5-indanyloxyalkanoic acid (XIV) with formaldehyde in the presence of a base such as sodium hydroxide and the like, followed by acifidication to afford the desired acid. The following equation illustrates this process:

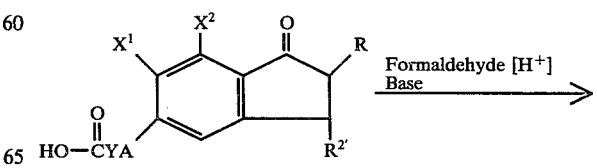

XIV

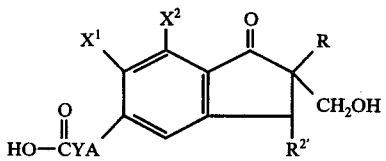

Ie wherein A, R, $R^{2'}$, $X^1$, $X^2$ and Y are as defined above. The 1-oxo-2-substituted-5-indanyloxyalkanoic acids are described in Great Britain Pat. No. 1,254,908.

Another method is to treat a 1-oxo-2-substituted-5-indanyloxyalkanoic acid with sodium alkoxide and methyl vinyl ketone in an inert atmosphere and then reducing the oxoalkyl substituent to a hydroxy alkyl with a reducing agent such as potassium borohydride.

The 1-oxo-2,2-disubstituted-5-indanyloxyalkanoic acids wherein $R^1$ is hydroxycycloalkyl are prepared generally by biological means. For example, to a typical cultured medium one can add a small amount of microorganism as a starter and after about 48 hours of culturing this broth medium compound of Formula I can then be added to the cultured medium. After a sufficient time for conversion, generally about 48 hours, the 1-oxo-2-(hydroxycycloalkyl)indanyloxyalkanoic acid can be extracted by acidifying the media and isolating the hydroxylated product along with some starting material in an organic solvent, generally a solvent which produces a 2 phase system. The 1-oxo-2-(hydroxycycloalkyl)indanyloxyalkanoic acid can then be separated from the starting material by thin layer chromatography. The culture medium can be any typical culture medium known to those skilled in the art whereas the microorganism which performs the conversion should generally be a fungal type rather than a bacterial type.

The 1-oxo-2,2-disubstituted-5-indanyloxyalkanoic acids wherein $R^1$ is alkoxyalkyl (If, infra) may be prepared by treating a correspondingly substituted hydroxyalkylindalyloxyalkanoic acid (Ie, supra) with a suitable alkylating agent such as isobutylene and the like followed by hydrolysis of the resultant ester. The following equation illustrates this process:

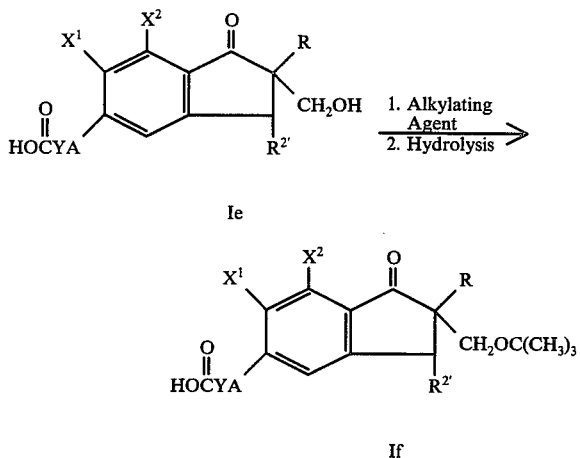

wherein R, $R^{2'}$, $X^1$, $X^2$, A and Y are as above defined.

The 1-oxo-2,2-disubstituted-3-halo-5-indanyloxy(or thio)-alkanoic acids (Ig, infra) may be prepared by treating a 1-oxo-2,2-disubstituted-5-indanyloxy(or thio)alkanoic acid (XV, infra) with a halogenating agent such as N-bromosuccinimide (NBS) and the like in a suitable inert solvent such as carbon tetrachloride and the like in the presence of a peroxide such as benzoylperoxide and the like. The following equation illustrates this process employing N-bromosuccinimide as the halogenating agent; however, it is to be understood that other equivalent halogenating agents may be employed:

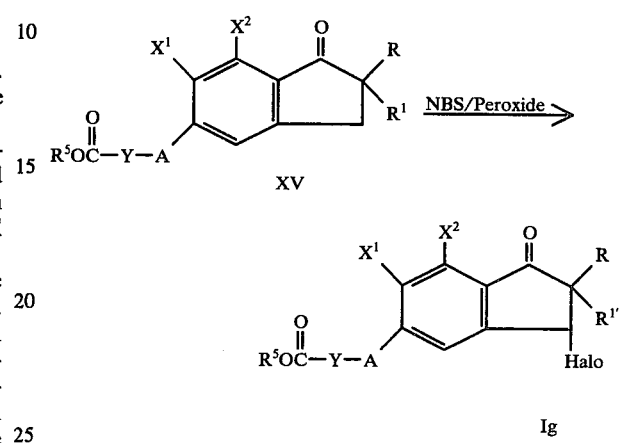

wherein A, R, $R^{1'}$, $R^5$, $X^1$, $X^2$ and Y are as defined above and halo is bromo, chloro and the like.

As previously mentioned, the non-toxic, pharmacologically acceptable salts of the acids of Compound I are within the scope of this invention and are prepared by conventional methods well known in the art. Thus, the acid upon reaction with alkali metal and alkaline earth metal hydroxides, carbonates, bicarbonates, amines or quarternary ammonium hydroxides, forms the corresponding alkali metal, alkaline earth metal, amine or quaternary ammonium salt. These salts are particularly useful as parenteral solutions because they are very soluble in pharmaceutical carriers such as water or alcohol.

The anhydride derived from the carboxylic acids of Formula I are included in the invention.

Also included within the scope of this invention are the ester and amide derivatives of the instant products which are prepared by conventional methods well known to those skilled in the art. Thus, for example, the ester derivative may be prepared by the reaction of a 1-oxo-2,2-disubstituted-5-indanyloxy(or thio)-alkanoic acid of this invention with an alcohol, for example, with a lower alkanol. The amide derivatives may be prepared by converting a 1-oxo-2,2-di-substituted-5-indanyloxy-(or thio)alkanoic acid to its corresponding acid chloride by treatment with thionyl chloride followed by treating said acid chloride with ammonia, an appropriate mono-lower alkyl amine, di-lower alkyl amine or a hetero amine, such as piperidine, morpholine and the like, to produce the corresponding amide compound. Included also are the N-amidino derivatives of the amides particularly the N-amidino indanyloxyacetamide derivative of the compounds of Formula I. These and other equivalent methods for the preparation of the ester and amide derivatives of the instant products will be apparent to one having ordinary skill in the art and to the extent that said derivatives are both non-toxic and physiologically acceptable to the body system, said derivatives are the functional equivalent of the corresponding 1-oxo-2,2-disubstituted-5-indanyloxy(or thio)alkanoic acids.

In addition to the salts, esters, anhydrides and amides being functionally equivalent to the carboxylic products, those compounds wherein the carboxylic acid is replaced by a 5-tetrazolyl radical are also functionally equivalent to the carboxylic acids. These tetrazole analogs are prepared as depicted in the following equation:

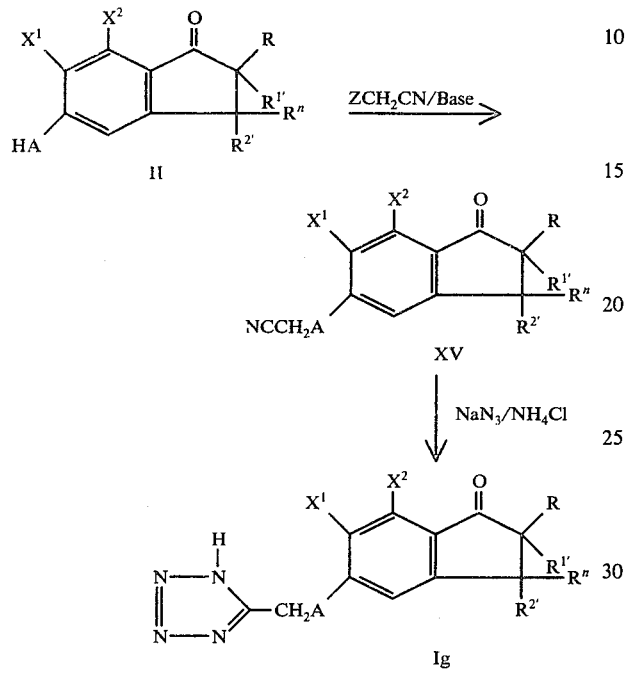

wherein A, R, R$^{1'}$, R$^{2'}$, R$^n$, X$^1$, X$^2$ and Z are as defined above.

The 2,2-disubstituted-5-hydroxy-1-indanone (II) is treated with a haloacetonitrile such as chloroacetonitrile, bromoacetonitrile or iodoacetonitrile in the presence of a base such as potassium carbonate and the like in a suitable solvent such as acetone, dimethylformamide, dimethoxyethane and the like at a temperature in the range of from 25° to 100° C. to afford the corresponding nitrile (XIV, supra) which, upon treatment with sodium azide and ammonium chloride in dimethylformamide at a temperature in the range of from 25° to 100° C., affords the 5-(1-oxo-2,2-disubstituted-5-indanyloxymethyl)tetrazole (Ig, supra).

Many of the instant compounds (I) herein disclosed contain an asymmetric carbon atom in the 2-position of the indanyl ring, i.e., alpha to the carbonyl group. When this situation exists, the optical antipodes may be separated by methods described above. This invention embraces, therefore, not only the racemic 1-oxo-2,2-disubstituted-5-indanyloxy(or thio)-alkanoic acids but also their optically active antipodes.

Separation of the optical isomers of the racemic acids (I) may be accomplished by forming a salt of the racemic mixture with an optically active base such as (+) or (−) amphetimine, (−)-cinchonidine, dehydroabietylamine, (+) or (−)-α-methylbenzylamine, (+) or (−)-α-(1-naphthyl)ethylamine, brucine or strychnine and the like in a suitable solvent such as methanol, ethanol, 2-propanol, benzene, acetonitrile, nitromethane, acetone and the like. There is thus formed in the solution two diastereomeric salts one of which is usually more soluble in the solvent than the other. Repetitive recrystallization of the crystalline salt generally affords a pure diastereomer. The optically pure 1-oxo-2,2-disubstituted-5-indanyloxy(or thio)alkanoic acid is obtained by acidification of the salt with a mineral acid, extraction into ether, evaporation of the solvent and recrystallization of the optically pure antipode.

The other optically pure antipode may generally be obtained by using a different base to form the diastereomeric salt. It is of advantage to isolate the partially resolved acid from the filtrates of the purification of the one diastereomeric salt and to further purify this substance through the use of another optically active base.

The examples which follow illustrate the 1-oxo-2,2-disubstituted-5-indanyloxy(or thio)alkanoic acid products (I) of the invention and the methods by which they are prepared. However, the examples are illustrative only and it will be apparent to those having ordinary skill in the art that all of the products embraced by formula I, supra, may also be prepared in an analogous manner by substituting the appropriate starting materials for those set forth in the examples.

EXAMPLE 1

[1'-Oxo-2-methyl-6',7'-dichlorospiro-(cyclopropane-1,2'-indan)-5'-yloxy]acetic Acid To a solution of (1-oxo-2-ethylidene-6,7-dichloro-5-indanyloxy)acetic acid (5.8 g., 0.0193 mole) in N,N-dimethylformamide (DMF) (50 ml.) is added sodium hydride (57% dispersion in mineral oil) (0.84 g.). The mixture is cooled in an ice bath and soon thickens. DMF (200 ml.) is added and the mixture is stirred for 1.5 hours at 20°–25° C. In a separate flask sodium hydride (57%, 1.5 g.) is added to DMF (50 ml.) and trimethylsulfoxonium iodide (8.2 g.) is added with stirring and cooling. The two mixtures are combined and stirred at 20°–25° C. for 2½ hours, poured into ice water (1.5 l.) and extracted with hexane. The aqueous phase is acidified with hydrochloric acid and extracted with ether (2 × 200 ml.) which is washed with water, dried over magnesium sulfate and evaporated at reduced pressure to obtain 6 g. of sticky yellow solid which after recrystallization from ethanol-water (1:1), acetic acid-water (1:1), and ethanol-water (1:1) gives 1.1 g. of [1'-oxo-2-methyl-6',7'-dichlorospiro-(cyclopropane-1,2'-indan)-5'-yloxy]acetic acid which melts at 90°–185° C. and is a mixture of the four isomers.

Elemental analysis for $C_{14}H_{12}Cl_2O_4$: Calc.: C, 53.36; H, 3.84; Found: C, 53.44; H, 3.82.

EXAMPLE 2

(1-Oxo-2-ethyl-2-hydroxymethyl-6,7-dichloro-5-indanyloxy)acetic Acid

To a solution of (1-oxo-2-ethyl-6,7-dichloro-5-indanyloxy)acetic acid (3.03 g., 0.01 mole) and sodium hydroxide (0.5 g., 0.0125 mole) in water (90 ml.) is added aqueous formaldehyde (1 ml., 0.012 mole). The resulting solution is stirred at 20°–25° C. for 4½ days and acidified with hydrochloric acid. The tan powder which precipitates is recrystallized from ethanol-water affording 1.2 g. of (1-oxo-2-ethyl-2-hydroxymethyl-6,7-dichloro-5-indanyloxy)acetic acid which melts at 155°–157° C.

Elemental analysis for $C_{14}H_{14}Cl_2O_5$: Calc.: C, 50.47; H, 4.24; Found: C, 50.62; H, 4.38.

EXAMPLE 3

(1-Oxo-2-hydroxymethyl-2-isopropyl-6,7-dichloro-5-indanyloxy)acetic Acid

To a solution of (1-oxo-2-isopropyl-6,7-dichloro-5-indanyloxy)acetic acid (3.17 g., 0.01 mole) and sodium hydroxide (0.5 g., 0.0125 mole) in water (90 ml.) is added aqueous formaldehyde (1 ml., 0.012 mole). The resulting solution is stirred at 20°–25° C. for 4½ days and acidified with hydrochloric acid. There is obtained 2.5 g. of (1-oxo-2-hydroxymethyl-2-isopropyl-6,7-dichloro-5-indanyloxy)acetic acid which melts at 200°–202° C. after recrystallization from ethanol-water.

Elemental analysis for $C_{15}H_{16}Cl_2O_5$: Calc.: C, 51.89; H, 4.65; Found: C, 51.46; H, 4.64.

EXAMPLE 4

(1-Oxo-2-ethyl-2-methyl-6,7-dichloro-5-indanyloxy)acetic Acid

Step A:
2-Ethyl-5-methoxy-6,7-dichloro-1-indanone

A stirred mixture of 2-ethyl-5-hydroxy-6,7-dichloro-1-indanone (18.3 g., 0.075 mole), potassium carbonate (23 g.) and methyl iodide (15 ml.) in DMF (100 ml.) is warmed at 55° C. for 2 hours and poured into water (300 ml.). The 2-ethyl-5-methoxy-6,7-dichloro-1-indanone which separates (18 g.) melts at 146°–147° C. after recrystallization from butyl chloride.

Elemental analysis for $C_{12}H_{12}Cl_2O_2$: Calc.: C, 55.62; H, 4.67; Found: C, 55.54; H, 4.55.

Step B:
2-Ethyl-2-methyl-5-methoxy-6,7-dichloro-1-indanone

Sodium hydride (2.1 g. of 57% oil dispersion, 0.05 mole) is washed with petroleum ether and transferred to a 1 l. flask under nitrogen with 1,2-dimethoxyethane (500 ml.) and 2-ethyl-5-methoxy-6,7-dichloro-1-indanone (13 g., 0.05 mole). The reaction mixture is refluxed in an inert atmosphere for two hours, cooled to 25° C., treated with methyl iodide (7 ml.), refluxed for ten minutes and poured into ice water (1.5 l.). The 2-ethyl-2-methyl-5-methoxy-6,7-dichloro-1-indanone which separates (12.0 g.) melts at 121° C. after recrystallization from methyl cyclohexane.

Elemental analysis for $C_{13}H_{14}Cl_2O_2$: Calc.: C, 57.16; H, 5.17; Found: C, 57.49; H, 5.18.

Step C:
2-Ethyl-2-methyl-5-hydroxy-6,7-dichloro-1-indanone

A mixture of 2-ethyl-2-methyl-5-methoxy-6,7-dichloro-1-indanone (5.4 g., 0.02 mole) and aluminum chloride (6.6 g., 0.05 mole) in heptane (180 ml.) is refluxed for one hour and cooled. The heptane is decanted and the product is scraped into ice water (100 ml.) and concentrated hydrochloric acid (10 ml.), extracted into ether (200 ml.), washed with water and dried over magnesium sulfate. The ether is evaporated and the product is recrystallized from butyl chloride (500 ml.) affording 3.7 g. of 2-ethyl-2-methyl-5-hydroxy-6,7-dichloro-1-indanone which melts at 215°–7° C.

Elemental analysis for $C_{12}H_{12}Cl_2O_2$: Calc.: C, 55.62; H, 4.67; Found: C, 55.79; H, 4.60.

Step D:
(1-Oxo-2-ethyl-2-methyl-6,7-dichloro-5-indanyloxy)acetic Acid

A stirred mixture of 2-ethyl-2-methyl-5-hydroxy-6,7-dichloro-1-indanone (3.6 g., 0.014 mole), potassium carbonate (4.2 g.), ethyl bromoacetate (5.0 g.) in DMF (40 ml.) is warmed in an inert atmosphere at 55° C. for 1 hour, then treated with water (40 ml.) and 10N sodium hydroxide (6 ml.) and heated on a steam bath for 1½ hours. The reaction mixture is poured into dilute aqueous hydrochloric acid, extracted with ether, washed with water and dried over magnesium sulfate. The ether is evaporated at reduced pressure affording the crude product which melts at 168° C. after recrystallization from nitromethane.

Elemental analysis for $C_{14}H_{14}Cl_2O_4$: Calc.: C, 53.02; H, 4.45; Found: C, 52.94; H, 4.45.

EXAMPLE 5

(1-Oxo-2,2-dimethyl-6,7-dichloro-5-indanyloxy)acetic Acid

Step A:
2',3'-Dichloro-4'-methoxyisobutyrophenone

A stirred mixture of 2,3-dichloroanisole (100 g., 0.565 mole) and isobutyryl chloride (66 g., 0.62 mole) in methylene chloride (400 ml.) is cooled to 5° C. and treated with aluminum chloride (83 g., 0.62 mole) during a one-hour period. The reaction mixture is allowed to warm to 25° C. and after 24 hours is poured into ice water (400 ml.) and hydrochloric acid (30 ml.). The organic phase is washed with 5% sodium hydroxide, water, dried over magnesium sulfate and distilled at reduced pressure affording 68 g. of 2',3'-dichloro-4'-methoxyisobutyrophenone which distills at 120°–130° C./0.5 mm.

Elemental analysis for $C_{11}H_{12}Cl_2O_2$: Calc.: C, 53.46; H, 4.89; Found: C, 54.25; H, 5.07.

Step B:
2-Bromo-2',3'-dichloro-4'-methoxyisobutyrophenone

A stirred solution of 2',3'-dichloro-4'-methoxyisobutyrophenone (45 g., 0.183 mole) in acetic acid (150 ml.) is treated during ½ hour with bromine (30 g., 0.187 mole). The reaction mixture is stirred 10 minutes, then poured into ice water (600 ml.) containing sodium bisulfite (2 g.). The 2-bromo-2',3'-dichloro-4'-methoxyisobutyrophenone which separates (48 g.) melts at 72°–73° C. after recrystallization from hexane.

Elemental analysis for $C_{11}H_{11}BrCl_2O_2$: Calc.: C, 40.52; H, 3.40; Found: C, 40.68; H, 3.38.

Step C:
2-Methylene-2',3'-dichloro-4'-methoxypropiophenone

A solution of 2-bromo-2',3'-dichloro-4'-methoxyisobutyrophenone (32 g., 0.1 mole) and anhydrous lithium bromide (17.4 g., 0.2 mole) in DMF (200 ml.) is stirred at 95° C. in an inert atmosphere for three hours and poured into ice water (500 ml.). The 2-methylene-2',3'-dichloro-4'-methoxypropiophenone which separates melts at 59° C. after recrystallization from petroleum ether.

Elemental analysis for $C_{11}H_{10}Cl_2O_3$: Calc: C, 53.90; H, 4.11; Found: C, 53.72; H, 4.11.

Step D: 2-Methyl-5-methoxy-6,7-dichloro-1-indanone

A solution of 2-methylene-2',3'-dichloro-4'-methoxypropiophenone (40 g., 0.163 mole) in concentrated sulfuric acid (75 ml.) is allowed to stand at 25° C. for 24 hours and then is slowly poured into vigorously stirred ice water (500 ml.). The 2-methyl-5-methoxy-6,7-dichloro-1-indanone which separates (40 g.) melts at 129° C. after recrystallization from methylcyclohexane.

Elemental analysis for $C_{11}H_{10}Cl_2O_2$: Calc.: C, 53.90; H, 4.11; Found: C, 53.84; H, 4.00.

Step E:
2,2-Dimethyl-5-methoxy-6,7-dichloro-1-indanone

A stirred suspension of 2-methyl-5-methoxy-6,7-dichloro-1-indanone (12.2 g., 0.05 mole) and sodium hydride (1.43 g., 0.06 mole) in anhydrous 1,2-dimethoxyethane (500 ml.) is heated in an inert atmosphere at 80°–85° C. for 1 hour, cooled to 30° C. and treated with methyl iodide (8 ml.) The reaction mixture is refluxed for 15 minutes, then the solvent is distilled at reduced pressure. The crude product is poured into water (500 ml.), extracted into ether, washed with water and dried over magnesium sulfate. After evaporation of the ether the product is crystallized from methylcyclohexane affording 8.2 g. of 2,2-dimethyl-5-methoxy-6,7-dichloro-1-indanone which melts at 142° C.

Elemental analysis for $C_{12}H_{12}Cl_2O_2$: Calc.: C, 55.62; H, 4.67; Found: C, 55.80; H, 4.69.

Step F:
2,2-Dimethyl-5-hydroxy-6,7-dichloro-1-indanone

A stirred suspension of 2,2-dimethyl-5-methoxy-6,7-dichloro-1-indanone (12.2 g., 0.047 mole) and aluminum chloride (15.5 g., 0.116 mole) in heptane (500 ml.) is refluxed for one hour and cooled. The heptane is decanted from the reaction mixture and the solid residue is poured into ice (500 g.) and concentrated hydrochloric acid (50 ml.). The product which separates (7.6 g.) melts at 273° C. after crystallization from nitromethane.

Elemental analysis for $C_{11}H_{10}Cl_2O_2$: Calc.: C, 53.90; H, 4.11; Found: C, 53.30; H, 4.12.

Step G:
(1-Oxo-2,2-dimethyl-6,7-dichloro-5-indanyloxy)acetic Acid

A stirred mixture of 2,2-dimethyl-5-hydroxy-6,7-dichloro-1-indanone (6.1 g., 0.025 mole), potassium carbonate (7.0 g.) and ethyl bromoacetate (8.3 g.) in DMF (65 ml.) is warmed in an inert atmosphere at 55° C. for 1 hour and then treated with water (70 ml.) and 10N sodium hydroxide (10 ml.) and heated on a steam bath for 2 hours. The reaction mixture is poured into water (300 ml.) containing hydrochloric acid (15 ml.). The (1-oxo-2,2-dimethyl-6,7-dichloro-5-indanyloxy)acetic acid which separates melts at 182° C. after recrystallization from nitromethane.

Elemental analysis for $C_{13}H_{12}Cl_2O_4$: Calc: C, 51.51; H, 3.99; Found: C, 51.27; H, 3.97.

EXAMPLE 6
(1-Oxo-2-ethyl-2-n-propyl-6,7-dichloro-5-indanyloxy)acetic Acid

Step A:
2-Ethyl-2-n-propyl-5-methoxy-6,7-dichloro-1-indanone

2-Ethyl-2-n-propyl-5-methoxy-6,7-dichloro-1-indanone is prepared following substantially the same procedure described in Example 5, Step E, using the following substances: 2-ethyl-5-methoxy-6,7-dichloro-1-indanone (13 g., 0.05 mole), sodium hydride (1.3 g., 0.055 mole), 1,2-dimethoxyethane (500 ml.) and n-propyliodide (6 ml.). The above procedure gives 6.0 g. of 2-ethyl-2-n-propyl-5-methoxy-6,7-dichloro-1-indanone which after recrystallization from ethanol melts at 92° C.

Elemental analysis for $C_{15}H_{18}Cl_2O_2$: Calc.: C, 59.81; H, 6.02; Found: C, 59.70; H, 5.90.

Step B:
2-Ethyl-2-n-propyl-5-hydroxy-6,7-dichloro-1-indanone

2-Ethyl-2-n-propyl-5-hydroxy-6,7-dichloro-1-indanone is prepared following substantially the same procedure described in Example 5, Step F, using the following substances: 2-ethyl-2-n-propyl-5-methoxy-6,7-dichloro-1-indanone (11 g., .037 mole), aluminum chloride (12.5 g., 0.094 mole) and heptane (400 ml.). The above procedure gives 9.0 g. of 2-ethyl-2-n-propyl-5-hydroxy-6,7-dichloro-1-indanone which after recrystallization from methylcyclohexane melts at 153° C.

Elemental analysis for $C_{14}H_{16}Cl_2O_2$: Calc.: C, 58.55; H, 5.62; Found: C, 58.54; H, 5.42.

Step C:
(1-Oxo-2-ethyl-2-n-propyl-6,7-dichloro-5-indanyloxy)acetic Acid (1-Oxo-2-ethyl-2-n-propyl-6,7-dichloro-5-indanyloxy)acetic acid is prepared following substantially the same procedure described in Example 5, Step G, using the following substances: 2-ethyl-2-n-propyl-5-hydroxy-6,7-dichloro-1-indanone (8.5 g., 0.03 mole), potassium carbonate (9 g.), ethyl bromoacetate (10.6 g.) and DMF (85 ml.). The above procedure gives 5.2 g. of (1-oxo-2-ethyl-2-n-propyl-6,7-dichloro-5-indanyloxy)acetic acid which melts at 126° C.

Elemental analysis for $C_{16}H_{18}Cl_2O_4$: Calc.: C, 55.67; H, 5.26; Found: C, 55.52; H, 5.31.

EXAMPLE 7
(1-Oxo-2-allyl-2-methyl-6,7-dichloro-5-indanyloxy)acetic Acid

Step A:
2-Allyl-2-methyl-5-methoxy-6,7-dichloro-1-indanone

2-Allyl-2-methyl-5-methoxy-6,7-dichloro-1-indanone is prepared following substantially the same procedure described in Example 5, Step E, using the following substances: 2-methyl-5-methoxy-6,7-dichloro-1-indanone (14.7 g., 0.06 mole), sodium hydride (1.7 g., 0.072 mole), 1,2-dimethoxyethane (500 ml.) and allyl bromide (8 ml.). The above procedure gives 11.0 g. of 2-allyl-2-methyl-5-methoxy-6,7-dichloro-1-indanone which after recrystallization from methyl cyclohexane melts at 58° C.

Elemental analysis for $C_{14}H_{14}Cl_2O_2$: Calc.: C, 58.97; H, 4.95; Found: C, 59.33; H, 5.13.

Step B:
2-Allyl-2-methyl-5-hydroxy-6,7-dichloro-1-indanone

A mixture of 2-allyl-2-methyl-5-methoxy-6,7-dichloro-1-indanone (4.0 g., 0.014 mole) and pyridine hydrochloride (40 g.) is heated at 185° C. for 1 hour, then poured into water. The 2-allyl-2-methyl-5-hydroxy-6,7-dichloro-1-indanone which separates (3.5 g.) melts at 180° C. after recrystallization from butyl chloride.

Elemental analysis for $C_{13}H_{12}Cl_2O_2$: Calc.: C, 57.55; H, 4.46; Found: C, 57.27; H, 4.50.

Step C:
(1-Oxo-2-allyl-2-methyl-6,7-dichloro-5-indanyloxy)acetic Acid

A stirred mixture of 2-allyl-2-methyl-5-hydroxy-6,7-dichloro-1-indanone (3.4 g., 0.0126 mole), potassium carbonate (4.2 g.) and ethyl bromoacetate (4.8 g.) in DMF (40 ml.) is warmed at 55° C. in an inert atmosphere, then treated with water (40 ml.) and 10N sodium hydroxide (2 ml.) and heated on a steam bath for one hour, poured into water (300 ml.), acidified and extracted with ether. The ether extract is washed with water, dried over magnesium sulfate and the solvent evaporated to leave a tan oil which is purified by chromatography over silica affording 2.0 g. of (1-oxo-2-allyl-2-methyl-6,7-dichloro-5-indanyloxy)acetic acid as a tan oil.

Elemental analysis for $C_{15}H_{14}Cl_2O_4$: Calc.: C, 54.73; H, 4.29; Found: C, 54.73; H, 4.65.

EXAMPLE 8

(1-Oxo-2,2-diethyl-6,7-dichloro-5-indanyloxy)acetic Acid

Step A:
2,2-Diethyl-5-methoxy-6,7-dichloro-1-indanone

A stirred suspension of 2-ethyl-5-methoxy-6,7-dichloro-1-indanone (7.8 g., 0.030 mole) and sodium hydride (750 mg., 0.031 mole) in 1,2-dimethoxyethane (200 ml.) is refluxed in an inert atmosphere for 1½ hours, cooled to 30° C., treated with ethyl iodide (5 ml.), refluxed for 1½ hours, then poured into ice water (700 ml.). The 2,2-diethyl-5-methoxy-6,7-dichloro-1-indanone which separates (7.5 g.) melts at 118° C. after recrystallization from methyl cyclohexane.

Elemental analysis for $C_{14}H_{16}Cl_2O_2$: Calc.: C, 58.55; H, 5.62; Found: C, 58.98; H, 5.57.

Step B: 2,2-Diethyl-5-hydroxy-6,7-dichloro-1-indanone

A stirred suspension of 2,2-diethyl-5-methoxy-6,7-dichloro-1-indanone (4.0 g., 0.014 mole) and aluminum chloride (4.7 g., 0.035 mole) in heptane (150 ml.) is refluxed for one hour and cooled. The heptane is decanted from the reaction mixture and the solid residue is treated with water (200 ml.) and concentrated hydrochloric acid (20 ml.). The 2,2-diethyl-5-hydroxy-6,7-dichloro-1-indanone which separates (3.7 g.) melts at 184° C. after recrystallization from butyl chloride.

Elemental analysis for $C_{13}H_{14}Cl_2O_2$: Calc.: C, 57.16; H, 5.17; Found: C, 57.08; H, 4.95.

Step C:
(1-Oxo-2,2-diethyl-6,7-dichloro-5-indanyloxy)acetic Acid

A stirred mixture of 2,2-diethyl-5-hydroxy-6,7-dichloro-1-indanone (3.6 g., 0.013 mole), potassium carbonate (4.2 g.) and ethyl bromoacetate (5 g.) in DMF (40 ml.) is warmed in an inert atmosphere at 55° C. for one hour, then treated with water (40 ml.) and 10N sodium hydroxide (6 ml.) and heated on a steam bath for 1.5 hours. The reaction mixture is poured into ice water (200 ml.), acidified, then extracted with ether, washed with water and dried over magnesium sulfate. Following evaporation of the ether the residue is crystallized from butyl chloride affording 1.3 g. of (1-oxo-2,2-diethyl-6,7-dichloro-5-indanyloxy)acetic acid which melts at 111° C.

Elemental analysis for $C_{15}H_{16}Cl_2O_4$: Calc.: C, 54.40; H, 4.87; Found: C, 54.46; H, 4.99.

EXAMPLE 9

(1-Oxo-2-isopropyl-2-methyl-6,7-dichloro-5-indanyloxy)acetic Acid

Step A:
2',3'-Dichloro-4'-methoxyisovalerophenone

A stirred mixture of 2,3-dichloroanisole (265 g., 1.50 mole) and isovaleryl chloride (200 g., 1.64 mole) in methylene chloride (1.2 l.) is cooled to 5° C. and treated with aluminum chloride (220 g., 1.64 mole) during a 2-hour period. The reaction is allowed to warm to 25° C. and after 24 hours is poured into ice water (3 l.) and hydrochloric acid (600 ml.). The organic phase is washed with 10% sodium hydroxide and water and dried over magnesium sulfate. After evaporation of the solvent, the product is crystallized from hexane affording 295 g. of 2',3'-dichloro-4'-methoxyisovalerophenone which melts at 49°-54° C.

Elemental analysis for $C_{12}H_{14}Cl_2O_2$: Calc.: C, 55.19; H, 5.40; Found: C, 55.38; H, 5.51.

Step B:
2-Methylene-2',3'-dichloro-4'-methoxyisovalerophenone

A stirred mixture of 2',3'-dichloro-4'-methoxyisovalerophenone (261.6 g., 1.0 mole), paraformaldehyde (75.0 g., 2.5 mole), dimethylamine hydrochloride (327 g., 4.0 mole) and acetic acid (26 ml.) is heated on a steam bath for 18 hours, treated with DMF (500 ml.), heated an additional 3 hours, then poured into ice water (1.7 l.). The crude product which separates is dissolved in benzene (600 ml.) and dried over sodium sulfate. Evaporation of the benzene affords 237 g. of 2-methylene-2',3'-dichloro-4'-methoxyiosovalerophenone which melts at 46°-51° C. and is used in Step C without further purification.

Step C:
2-Isopropyl-5-methoxy-6,7-dichloro-1-indanone

A solution of the product of Step B (237 g.) in concentrated sulfuric acid (400 ml.) is stirred at 25° C. for two hours, then slowly added to a copious amount of ice water. The product which separates is triturated with fresh water, neutralized with aqueous sodium bicarbonate, filtered and dried. Recrystallization from benzene-hexane affords 134 g. of 2-isopropyl-5-methoxy-6,7-dichloro-1-indanone which melts at 118°-119° C.

Elemental analysis for $C_{13}H_{14}Cl_2O_2$: Calc.: C, 57.16; H, 5.17; Found: C, 57.23; H, 5.33.

Step D:
2-Methyl-2-isopropyl-5-methoxy-6,7-dichloro-1-indanone

A stirred suspension of 2-isopropyl-5-methoxy-6,7-dichloro-1-indanone (7.3 g., 0.025 mole) and sodium hydride (810 mg., 0.028 mole) in anhydrous 1,2-dimethoxyethane (250 ml.) is heated in an inert atmosphere at 80°-85° C. for 1 hour, cooled to 30° C. and treated with methyl iodide (6 ml.). The reaction mixture is heated to 80° C., then the solvent is distilled at reduced pressure and the residue poured into ice water. The 2-methyl-2-isopropyl-5-methoxy-6,7-dichloro-1-indanone which separates (7.0 g.) melts at 143° C. after recrystallization from ethanol-water.

Elemental analysis for $C_{14}H_{16}Cl_2O_2$: Calc.: C, 58.55; H, 5.62; Found: C, 58.82; H, 5.60.

Step E:
2-Methyl-2-isopropyl-5-hydroxy-6,7-dichloro-1-indanone

A stirred suspension of 2-methyl-2-isopropyl-5-methoxy-6,7-dichloro-1-indanone (7.0 g., 0.0244 mole) and aluminum chloride (9.0 g., 0.068 mole) in heptane (400 ml.) is refluxed for one hour and cooled. The heptane is decanted from the reaction mixture and the solid residue is poured into water (300 ml.) and concentrated hydrochloric acid (20 ml.). The crude product is extracted into ether (300 ml.), washed with water, dried over magnesium sulfate, distilled to a volume of 100 ml. and treated with hexane (100 ml.). The 2-methyl-2-isopropyl-5-hydroxy-6,7-dichloro-1-indanone which separates (6.5 g.) melts at 215° C.

Elemental analysis for $C_{13}H_{14}Cl_2O_2$: Calc.: C, 57.16; H, 5.17; Found: C, 56.90; H, 5.15.

Step F:
(1-Oxo-2-methyl-2-isopropyl-6,7-dichloro-5-indanyloxy)acetic Acid

A stirred mixture of 2-methyl-2-isopropyl-5-hydroxy-6,7-dichloro-1-indanone (6.2 g., 0.023 mole), potassium carbonate (7.3 g.), ethyl bromoacetate (8.5 g.) in DMF (70 ml.) is warmed in an inert atmosphere at 55° C. for 1 hour, then treated with water (60 ml.) and 10N sodium hydroxide (10 ml.) and heated on a steam bath for 1.5 hours. The reaction mixture is poured into water, acidified, extracted with ether, washed with water and dried over magnesium sulfate. Following evaporation of the ether there is obtained 5.1 g. of (1-oxo-2-methyl-2-isopropyl-6,7-dichloro-5-indanyloxy)acetic acid which melts at 156°-157° C. after recrystallization from nitromethane.

Elemental analysis for $C_{15}H_{16}Cl_2O_4$: Calc.: C, 54.40; H, 4.87; Found: C, 53.99; H, 4.77.

EXAMPLE 10
(1-Oxo-2-cyclopentyl-2-methyl-6,7-dichloro-5-indanyloxy)acetic Acid

Step A:
2',3'-Dichloro-4'-methoxy-2-cyclopentylacetophenone 2,3-Dichloroanisole (57.8 g., 0.327 mole) is dissolved in dichloromethane (300 ml.) and cyclopentylacetyl chloride (52.7 g., 0.367 mole) is added. The solution is cooled to +5° C. and aluminum chloride (48.0 g., 0.36 mole) is added gradually over a one-hour period at +5° C. The mixture is stirred for two hours at +5° C. and at 20°-25° C. for 16 hours and then poured into 1 l. of ice water containing 150 ml. of 12N hydrochloric acid. The organic phase is separated and the aqueous phase is extracted with dichloromethane. The combined organic phases are washed with sodium chloride solution, 10% sodium hydroxide and again with sodium chloride solution and dried over magnesium sulfate. On evaporation of the solvent a brown solid is obtained which is crystallized from hexane to obtain 53.2 g. of 2',3'-dichloro-4'-methoxy-2-cyclopentylacetophenone, m.p. 60°-61.5° C.

Elemental analysis for $C_{15}H_{16}Cl_2O_2$: Calc.: C, 58.55; H, 5.62; Found: C, 58.72; H, 5.71.

Step B:
4'-(2-Cyclopentyl-2-methyleneacetyl)-2',3'-dichloroanisole

2',3'-Dichloro-4'-methoxy-2-cyclopentylacetophenone (51.6 g., 0.18 mole) is dissolved in dioxane (460 ml.) and paraformaldehyde (21.6 g., 0.72 mole) and concentrated sulfuric acid (9.65 g.) are added. The mixture is heated at 80°-85° C. for 20 hours. The dioxane is evaporated at reduced pressure. Water is added to the residual gum which then is extracted into ether. The ether extract is washed with water and dried over magnesium sulfate. The ether is evaporated and upon triturating the residue with hexane (5 ml.) there is obtained a solid that is crystallized from ligroin to obtain 4'-(2-cyclopentyl-2-methyleneacetyl)-2',3'-dichloroanisole (33.3 g.), m.p. 59°-63° C. Crystallization from butyl chloride affords a sample (m.p. 66°-67.5° C.) for analysis.

Elemental analysis for $C_{16}H_{16}Cl_2O_2$: Calc.: C, 60.21; H, 5.37; Found: C, 60.19; H, 5.42.

Step C:
2-Cyclopentyl-5-methoxy-6,7-dichloro-1-indanone

4'-(2-Cyclopentyl-2-methyleneacetyl)-2',3'-dichloroanisole (33.3 g.) is dissolved in 98% sulfuric acid (150 ml.) and stirred at 20° C. for 1.5 hours. The solution then is added dropwise with stirring to ice water. The aqueous phase is decanted from the gummy product and fresh water is added. After 20 hours the gum solidifies and is crystallized from hexane-benzene (3:1) to obtain 2-cyclopentyl-5-methoxy-6,7-dichloro-1-indanone, m.p. 116°-117° C.

Elemental analysis for $C_{16}H_{16}Cl_2O_2$: Calc.: C, 60.21; H, 5.37; Found: C, 60.29; H, 5.35.

Step D:
2-Cyclopentyl-2-methyl-5-methoxy-6,7-dichloro-1-indanone

2-Cyclopentyl-5-methoxy-6,7-dichloro-1-indanone (7.5 g., 0.025 mole) is dissolved in dry 1,2-dimethoxyethane (200 ml.) under nitrogen. Sodium hydride (57% in mineral oil; 1.16 g., 0.0275 mole) is then added and the mixture is stirred at 80° until evolution of hydrogen ceases (2 hours). The solution is cooled and methyl iodide (7.5 ml.) is added, the mixture is again brought to reflux and then cooled. Most of the 1,2-dimethoxyethane is evaporated and water is added to the residue which soon solidifies and is crystallized from methylcyclohexane and from ethanol-water (4:1) to obtain 3.4 g. of 2-cyclopentyl-2-methyl-5-methoxy-6,7-dichloro-1-indanone, m.p. 109°-111.5° C.

Elemental analysis for $C_{17}H_{18}Cl_2O_2$: Calc.: C, 61.35; H, 5.79; Found: C, 61.71; H, 5.84.

Step E:
2-Cyclopentyl-2-methyl-5-hydroxy-6,7-dichloro-1-indanone

2-Cyclopentyl-2-methyl-5-methoxy-6,7-dichloro-1-indanone (3.4 g., 0.0109 mole) is added to dry heptane (180 ml.) and aluminum chloride (4.36 g., 0.0327 mole) is added. The mixture is refluxed for 1 hour and the hexane is decanted from the gummy residue which then is added to ice water (200 ml.) containing 12N hydrochloric acid (15 ml.). The solid that separates is crystallized from benzene to obtain 2.77 g. of 2-cyclopentyl-2-methyl-5-hydroxy-6,7-dichloro-1-indanone, m.p. 190°-194° C.

Elemental analysis for $C_{16}H_{16}Cl_2O_2$: Calc.: C, 60.21; H, 5.37; Found: C, 60.43; H, 5.41.

Step F:
(1-Oxo-2-cyclopentyl-2-methyl-6,7-dichloro-5-indanyloxy)acetic Acid 2-Cyclopentyl-2-methyl-5-hydroxy-6,7-dichloro-1-indanone (2.77 g., 0.00926 mole) is added to dimethylformamide (DMF) (40 ml.). Potassium carbonate (3.21 g., 0.0232 mole) and ethyl bromoacetate (3.34 g., 0.0232 mole) are added. The mixture is stirred at 55°–60° C. for 2½ hours, then 40 ml. of 10% sodium hydroxide are added and the mixture is stirred at 80°–85° C. for 1½ hours. The mixture then is added to 500 ml. of 2% hydrochloric acid. The solid that separates is taken up in ether. The ether extract is washed with water, dried over magnesium sulfate and evaporated, leaving a gummy solid that is crystallized from acetic acid to obtain 950 mg. of (1-oxo-2-cyclopentyl-2-methyl-6,7-dichloro-5-indanyloxy)acetic acid which melts at 113°–114° C. (1-Oxo-2-cyclopentyl-2-methyl-6,7-dichloro-5-indanyloxy)acetic acid also has an allotropic form which melts at 139.5°–141° C.

Elemental analysis for $C_{17}H_{18}Cl_2O_4$: Calc.: C, 57.16; H, 5.08 Found: C, 57.29; H, 5.34

EXAMPLE 11
Process for preparing (1-oxo-2-cyclopentyl-2-methyl-6,7-dichloro-5-indanyloxy)acetic acid

Step A:
2-Cyclopentyl-2-methyl-5-methoxy-6,7-dichloro-1-indanone

A solution of 2-methyl-5-methoxy-6,7-dichloro-1-indanone (7.35 g., 0.03 mole) in tert.-butyl alcohol (100 ml.) is refluxed in an inert atmosphere and treated with potassium tert.-butoxide (4.48 G., 0.04 mole). After one-half hour at reflux cyclopentyl bromide (9.9 g., 0.06 mole) is added and refluxing is continued for 1 hour. The reaction is poured into water (1 l.) affording 2-cyclopentyl-2-methyl-5-methoxy-6,7-dichloro-1-indanone which melts at 109°–111° C.

Step B:
2-Cyclopentyl-2-methyl-5-hydroxy-6,7-dichloro-1-indanone

2-Cyclopentyl-2-methyl-5-methoxy-6,7-dichloro-1-indanone (3.4 g., 0.0109 mole) is added to dry heptane (180 ml.) and aluminum chloride (4.36 g., 0.0327 mole) is added. The mixture is refluxed for 1 hour and the hexane is decanted from the gummy residue which then is added to ice water (200 ml.) containing 12N hydrochloric acid (15 ml.). The solid that separates is crystallized from benzene to obtain 2.77 g. of 2-cyclopentyl-2-methyl-5-hydroxy-6,7-dichloro-1-indanone, m.p. 190°–194° C.

Elemental analysis for $C_{16}H_{16}Cl_2O_2$: Calc.: C, 60.21, H, 5.37 Found: C, 60.43, H, 5.41

Step C: Tert-butyl (1-oxo-2-cyclopentyl-2-methyl-6,7-dichloro-5-indanyloxy)acetate A mixture of 2-cyclopentyl-2-methyl-5-hydroxy-6,7-dichloro-1-indanone (2.98 g., 0.01 mole), tert.-butylbromoacetate (2.15 g., 0.011 mole), potassium carbonate (2.76 g., 0.02 mole) and dimethylformamide (15 ml.) is stirred at 25° for 1 hour then poured into water (50 ml.) the tert.-butyl (1-oxo-2-cyclopentyl-6,7-dichloro-5-indanyloxy)acetate which separates is filtered, rinsed with water and dried.

Step D:
(1-Oxo-2-cyclopentyl-2-methyl-6,7-dichloro-5-indanyloxy)acetic acid A solution of tert.-butyl (1-oxo-2-cyclopentyl-2-methyl-6,7-dichloro-5-indanyloxy)acetate (4.13 g., 0.01 mole) and p-toluenesulfonic acid (0.3 g.) in benzene (50 ml.) is refluxed for ten minutes then cooled to 25° C. affording (1-oxo-2-cyclopentyl-2-methyl-6,7-dichloro-5-indanyloxy)acetic acid which melts at 113°–114° C. after recrystallization from acetic acid.

EXAMPLE 12
(1-Oxo-2-benzyl-2-methyl-6,7-dichloro-5-indanyloxy)acetic acid

Step A:
2-Benzyl-2-methyl-5-methoxy-6,7-dichloro-1-indanone

Potassium tert-butoxide (1.68 g., 0.015 mole) in dry tert-butyl alcohol (40 ml.) is added to a refluxing solution of 2-methyl-5-methoxy-6,7-dichloro-1-indanone in benzene (50 ml.). After refluxing for 30 minutes, benzyl bromide (1.72 g., 0.01 mole) in benzene (10 ml.) is added dropwise. After refluxing for an additional 30 minutes the mixture is cooled, water (10 ml.) is added and the mixture is evaporated to dryness. The residue is washed with water and taken up in ether. The ether solution is washed with water and a saturated sodium chloride solution, dried over solium sulfate and evaporated. The syrupy residue is 2-benzyl-2-methyl-5-methoxy-6,7-dichloro-1-indanone (3 g.) is used directly in the next step without purification.

Step B:
2-Benzyl-2-methyl-5-hydroxy-6,7-dichloro-1-indanone

2-Benzyl-2-methyl-5-methoxy-6,7-dichloro-1-indanone (6 g.) is mixed with pyridine hydrochloride (60 g.) and the mixture is heated at 180° C. for 3 hours. The dark liquid is poured into water (1 l.) and the dark powdery product is collected and crystallized from acetic acid to obtain 2-benzyl-2-methyl-5-hydroxy-6,7-dichloro-1-indanone (2 g.), m.p. 219°–221° C. The product is identified by its nuclear magnetic resonance spectrum.

NMR: (DMSO-$D_6$) — $\delta$11.5 (1S— —OH); $\delta$7.2 (5S — aromatic); $\delta$6.9 (1S — aromatic); $\delta$1.1 (3S— —$CH_3$).

Step C:
(1-Oxo-2-benzyl-2-methyl-6,7-dichloro-5-indanyloxy)acetic Acid 2-Benzyl-2-methyl-5-hydroxy-6,7-dichloro-1-indanone (2 g., 0.0062 mole) is dissolved in dimethylformamide (DMF) (20 ml.) and potassium carbonate (1 g., 0.007 mole) is added. The mixture is stirred at 60° C. for 20 minutes and then ethyl bromoacetate (1.17 g., 0.007 mole) is added and the mixture is stirred at 60° C. for 2 hours. A solution of potassium hydroxide (0.56 g., 0.01 mole) in methanol (50 ml.) is added. The mixture is refluxed for 178 hour and poured into water (500 ml.). The solution is filtered and acidified with hydrochloric acid. The oil that separates is extracted with ether. The ether extract is washed with water, dried over magnesium sulfate and evaporated. The residue solidifies on trituration with butyl chloride and is crystallized from acetic acid-water (1:1) to obtain 1.1 g. of (1-oxo-2-benzyl-2-methyl-6,7-dichloro-5-indanyloxy)acetic acid, m.p. 167°–168° C.

Elemental analysis for $C_{19}H_{16}Cl_2O_4$: Calc.: C, 60.18; H, 4.25; Found: C, 60.13; H, 4.33.

EXAMPLE 13

[1'-Oxo-6',7'-dichlorospiro-(cyclopentane-1,2'-indan)-5'-yloxy]acetic acid

Step A:
2,3-Dichloro-4-(6-bromohexanoyl) anisole

A stirred mixture of 2,3-dichloroanisole (89 g., 0.50 mole) and 6-bromohexanoylchloride (120 g., 0.59 mole) in methylene chloride (500 ml.) is cooled to 5° C. and treated with aluminum chloride (74 g., 0.56 mole) in portions during a one-half hour period. The reaction mixture is kept at 25° C. for 18 hours then poured into ice water (1 l.) containing hydrochloric acid (100 ml.) the organic phase is separated, washed with water, 2% sodium hydroxide and dilute hydrochloric acid. The methylene chloride is evaporated at reduced pressure. The crude product is dissolved in ether (200 ml.), dried over magnesium sulfate, filtered and treated with hexane (600 ml.) affording 2,3-dichloro-4-(6-bromohexanoyl)anisole which melts at 52°–53° C.

Elemental Analysis for $C_{13}H_{15}BrCl_2O_2$: Calc.: C, 44.10; H, 4.27 Found: C, 44.33; H, 4.16

Step B:
2-(4-Chlorobutyl)-5-methoxy-6,7-dichloro-1-indanone

A stirred mixture of 2,3-dichloro-4-(6-bromohexanoyl)anisole (10 g.), dimethylamine hydrochloride (4 g.), paraformaldehyde (2 g.) and acetic acid (0.5 ml.) is heated on a steam bath for two hours, treated with DMF (30 ml.) and heated an additional 2½ hours. The reaction mixture is poured into water, extracted with ether, washed with water and dried over magnesium sulfate. Evaporation of the ether affords 9 g. of crude 2,3-dichloro-4-(6-chloro-2-methylenehexanoyl)anisole which is cyclialkylated by treatment with concentrated sulfuric acid (50 ml.). The sulfuric acid solution is poured into water (300 ml.) affording 5.8 g. of 2-(4-chlorobutyl)-5-methoxy-6,7-dichloro-1-indanone which melts at 92° C. after recrystallization from cyclohexane.

Elemental analysis for $C_{14}H_{15}Cl_3O_2$: Calc.: C, 52.28; H, 4.70; Cl, 33.07; Found: C, 52.25; H, 4.50; Cl, 33.03.

Step C:
5'-Methoxy-6',7'-dichlorospiro-(cyclopentane-1,2'-indanone)

A stirred suspension of sodium hydride (370 mg., 0.0155 mole) in 1,2-dimethoxyethane (250 ml.) is refluxed in an inert atmosphere. A solution of 2-(4-chlorobutyl)-5-methoxy-6,7-dichloro-1-indanone (4.5 g., 0.014 mole) in 1,2-dimethoxyethane (50 ml.) is added over a 20-minute period and refluxing is maintained for 3 hours. The solvent is distilled to a volume of 50 ml. and poured into water (300 ml.) affording 2.6 g. of 5'-methoxy-6',7'-dichlorospiro(cyclopentane-1,2'-indanone) which melts at 170° C. after recrystallization from ethanol-water.

Elemental analysis for $C_{14}H_{14}Cl_2O_2$: Calc.: C, 58.97; H, 4.95; Found: C, 59.34; H, 5.08.

Step D:
5'-Hydroxy-6',7'-dichlorospiro-(cyclopentane-1,2'-indanone)

A stirred mixture of 5'-methoxy-6',7'-dichlorospiro(cyclopentane-1,2'-indanone) (2.6 g., 0.0091 mole) and pyridine hydrochloride (26 g.) is heated at 185° C. for 1 hour, then poured into water (200 ml.). The 5'-hydroxy-6',7'-dichlorospiro-(cyclopentane-1,2'-indanone) which separates (2.3 g.) melts at 236° C. after recrystallization from nitromethane.

Elemental analysis for $C_{13}H_{12}Cl_2O_2$: Calc.: C, 57.55; H, 4.46; Found: C, 57.77; H, 4.54.

Step E:
[1'-Oxo-6',7'-dichlorospiro (cyclopentane-1,2'-indan)-5'-yloxy]acetic Acid

[1'-Oxo-6',7'-dichlorosporo-(cyclopentane-1,2'-indan)-5'-yloxy]acetic acid is prepared following substantially the same procedure described in Example 5, Step G, using the following substances: 5'-hydroxy-6',7'-dichlorospiro-(cyclopentane-1,2'-indanone) (2.3 g., 0.0085 mole), potassium carbonate (2.7 g.), ethyl bromoacetate (2.1 ml.) and DMF (25 ml.). The above procedure gives 2.7 g. (96%) of [1'-oxo-6',7'-dichlorospiro-(cyclopentane-1,2'-indan)-5'-yloxy]acetic acid which after recrystallization from nitromethane melts at 195° C.

Elemental analysis for $C_{15}H_{14}Cl_2O_4$: Calc.: C, 54.73; H, 4.29; Found: C, 55.00; H, 4.25.

EXAMPLE 14

[1-Oxo-2-(2-chloroallyl)-2-methyl-6,7-dichloro-5-indanyloxy]acetic Acid

Step A:
2-Methyl-2-propargyl-5-methoxy-6,7-dichloro-1-indanone

2-Methyl-2-propargyl-5-methoxy-6,7-dichloro-1-indanone is prepared by following substantially the same procedure described in Example 4, Step B, using the following reagents: 2-methyl-5-methoxy-6,7-dichloro-1-indanone (14.7 g., 0.06 mole), sodium hydride (1.72 g., 0.072 mole), 1,2-dimethoxyethane (500 ml.) and propargyl bromide (8 ml.). The above procedure gives 16.5 g. (97%) of 2-methyl-2-propargyl-5-methoxy-6,7-dichloro-1-indanone which after recrystallization from methyl cyclohexane melts at 118° C.

Elemental analysis for $C_{14}H_{12}Cl_2O_2$: Calc.: C, 59.39; H, 4.27; Found: C, 59.76; H, 4.40.

Step B:
2-(2-Chloroallyl)-2-methyl-5-hydroxy-6,7-dichloro-1-indanone

A stirred mixture of 2-methyl-2-propargyl-5-methoxy-6,7-dichloro-1-indanone (11 g., 0.039 mole) and pyridine hydrochloride (110 g.) is heated at 185° C. for one hour, then poured into water (500 ml.). The product which separates is recrystallized from ethanol-water affording 6.5 g. of 2-(2-chloroallyl)-2-methyl-5-hydroxy-6,7-dichloro-1-indanone, m.p. 183° C.

Step C:
[1-Oxo-2-(2-chloroallyl)-2-methyl-6,7-dichloro-5-indanyloxy]acetic Acid

[1-Oxo-2-(2-chloroallyl)-2-methyl-6,7-dichloro-5-indanyloxy]acetic acid is prepared following substantially the same procedure described in Example 4, Step D, using the following reagents: 2-(2-chloroallyl)-2-methyl-5-hydroxy-6,7-dichloro-1-indanone (4.8 g., 0.0157 mole), potassium carbonate (6.0 g.), ethyl bromoacetate (4.5 ml.) and DMF (55 ml.). The above procedure gives 2.7 g. (48%) of [1-oxo-2-(2-chloroallyl)-2-methyl-6,7-dichloro-5-indanyloxy]acetic acid which after recrystallization from butyl chloride melts at 160°–162° C.

Elemental analysis for $C_{15}H_{13}Cl_3O_4$: Calc.: C, 49.54; H, 3.60; Cl, 29.25; Found: C, 49.31; H, 3.55; Cl, 29.26

EXAMPLE 15

[1'-Oxo-6',7'-dichlorospiro-(cyclohexane-1,2'-indan)-5'-yloxy]acetic acid

Step A: 2,3-Dichloro-4-(7-bromoheptanoyl)anisole

The title compound is prepared following substantially the same procedure described in Example 13, Step A, using the following substances: 2,3-dichloroanisole (89 g., 0.5 mole), 7-bromoheptanoyl chloride (127 g., 0.56 mole), aluminum chloride (74 g., 0.56 mole) and methylene chloride (500 ml.). This procedure affords 107 g. (58%) of 2,3-dichloro-4-(7-bromoheptanoyl)anisole which after recrystallization from cyclohexane melts at 57° C.

Elemental analysis for $C_{14}H_{17}BrCl_2O_2$: Calc.: C, 45.68; H, 4.65 Found: C, 45.53; H, 4.66

Step B: 2-(5-Chloropentyl)-5-methoxy-6,7-dichloro-1-indanone

The title compound is prepared following substantially the same procedure described in Example 13, Step B, using the following substances: 2,3-dichloro-4-(7-bromoheptanoyl)anisole (22.5 g., 0.06 mole), dimethylamine hydrochloride (22.5 g.), paraformaldehyde (4.7 g.), acetic acid (1.8 ml.) and the crude α,β-unsaturated ketone thus obtained is cyclialkylated in sulfuric acid (100 ml.). This procedure affords 15 g. of 2-(5-chloropentyl)-5-methoxy-6,7-dichloro-1-indanone which after recrystallization from benzene-hexane melts at 115° C.

Elemental analysis for $C_{15}H_{17}Cl_3O_2$: Calc.: C, 53.67; H, 5.10; Cl, 31.69 Found: C, 53.39; H, 5.15; Cl, 31.36

Step C: 5'-Methoxy-6',7'-dichlorospiro-(cyclohexane-1,2'-indanone)

The title compound is prepared following substantially the same procedure described in Example 12, Step A, using the following substances: 2-(5-chloropentyl)-5-methoxy-6,7-dichloro-1-indanone (11 g., 0.0289 mole), benzene (150 ml.), tert-butanol (100 ml.) and potassium tert-butoxide (4.86 g.). This procedure affords 8.6 g. (100%) of 5'-methoxy-6',7'-dichlorospiro-(cyclohexane-1,2'-indanone) which after recrystallization from butyl chloride melts at 210° C.

Elemental analysis for $C_{15}H_{16}Cl_2O_2$: Calc.: C, 60.21; H, 5.39 Found: C, 60.37; H, 5.46

Step D: 5'-Hydroxy-6',7'-dichlorospiro-(cyclohexane-1,2'-indanone)

The title compound is prepared following substantially the same procedure described in Example 13, Step D, using the following substances: 5'-methoxy-6',7'-dichlorospiro-(cyclohexane-1,2'-indanone) (9.0 g.) and pyridine hydrochloride (90 g.). This procedure affords 8.0 g. (93%) of 5'-hydroxy-6',7'-dichlorospiro-(cyclohexane-1,2'-indanone) which after recrystallization from ethanol melts at 268°–270° C.

Elemental analysis for $C_{14}H_{14}Cl_2O_2$: Calc.: C, 58.96; H, 4.95 Found: C, 59.08; H, 5.01

Step E: [1'-Oxo-6',7'-dichlorospiro-(cyclohexane-1,2'-indan)-5'-yloxy]acetic acid The title compound is prepared following substantially the same procedure described in Example 5, Step G, using the following substances: 5'-hydroxy-6',7'-dichlorospiro-(cyclohexane-1,2'-indanone) (8.0 g.), potassium carbonate (7.0 g.), ethyl bromoacetate (6.0 ml.) and dimethylformamide (60 ml.). This procedure affords 7.0 g. (73%) of [1'-oxo-6',7'-dichlorospiro-(cyclohexane-1,2'-indan)-5'-yloxy]acetic acid which after recrystallization from nitromethane melts at 225° C.

Elemental analysis for $C_{16}H_{16}Cl_2O_4$: Calc.: C, 55.99; H, 4.70 Found: C, 55.69; H, 4.73

EXAMPLE 16

5-(1-Oxo-2-isopropyl-2-methyl-6,7-dichloro-5-indanyloxymethyl)-tetrazole

Step A: (1-Oxo-2-isopropyl-2-methyl-6,7-dichloro-5-indanyloxy)acetonitrile

A stirred mixture of 2-isopropyl-2-methyl-5-hydroxy-6,7-dichloro-1-indanone (8.2 g., 0.03 mole), potassium carbonate (4.15 g. 0.03 mole), chloroacetonitrile (2.4 g., 0.032 mole) and potassium iodide (0.5 g.) in acetone is refluxed for 18 hours. The solvent is evaporated and the residue is treated with water (100 ml.) affording 8.0 g. of (1-oxo-2-isopropyl-2-methyl-6,7-dichloro-5-indanyloxy) acetonitrile which melts at 133° C. After recrystallization from butyl chloride.

Elemental analysis for $C_{15}H_{15}Cl_2NO_2$: Calc.: C, 57.71; H, 4.84; N, 4.49; Found: C, 57.53; H, 4.72; N, 4.57.

Step B: 5-(1-Oxo-2-isopropyl-2-methyl-6,7-dichloro-5-indanyloxymethyl)tetrazole A stirred solution of (1-oxo-2-isopropyl-2-methyl-6,7-dichloro-5-indanyloxy)acetonitrile (6.2 g., 0.02 mole), sodium azide (1.55 g., 0.024 mole) and ammonium chloride (1.24 g., 0.023 mole) in DMF (30 ml.) is heated in an inert atmosphere for one hour, poured into water (200 ml.) and acidified with hydrochloric acid. The 5-(1-oxo-2-isopropyl-2-methyl-6,7-dichloro-5-indanyloxymethyl) tetrazole which separates (4.2 g.) melts at 173° C. after recrystallization from methanol-water.

Elemental anayslsis for $C_{15}H_{16}Cl_2N_4O_2$: Calc.: C, 50.72; H, 4.54; N, 15.77; Found: C, 50.53; H, 4.36; N, 15.66.

EXAMPLE 17

(1-Oxo-2-cyclopentyl-2,6-dimethyl-7-chloro-5-indanyloxy)acetic Acid

Step A: 2'-Chloro-3'-methyl-4'-methoxy-2-cyclopentylacetophenone

By following substantially the procedure described in Example 9, Step A, using the following substances: 2-methyl-3-chloroanisole (36.5 g., 0.234 mole), cyclopentylacetyl chloride (37.7 g., 0.257 mole), aluminum chloride (34.3 g., 0.257 mole) and methylene chloride (250 ml.) there is obtained 50 g. (80%) of 2'-chloro-3'-methyl-4'-methoxy-2-cyclopentylacetophenone which distills at 145°–165° C./0.6 mm.

Elemental analysis for $C_{15}H_{19}ClO_2$: Calc.: C, 67.54; H, 7.18; Found: C, 67.53; H, 7.41.

Step B:
2'-Chloro-3'-methyl-4'-methoxy-2-cyclopentylacrylophenone

By following substantially the procedure described in Example 9, Step B, using the following substances: 2'-chloro-3'-methyl-4'-methoxy-2-cyclopentylacetophenone (45 g., 0.169 mole), paraformaldehyde (12.6 g., 0.42 mole), dimethylamine hydrochloride (61 g., 0.75 mole) and acetic acid (4.2 ml.) there is obtained 36.3 g. (78%) of 2'-chloro-3'-methyl-4'-methoxy-2-cyclopentylacrylophenone which after recrystallization from petroleum ether melts at 45°–46.5° C.

Elemental analysis for $C_{16}H_{19}ClO_2$: Calc.: C, 68.93; H, 6.87; Found: C, 69.02; H, 6.96.

Step C:
2-Cyclopentyl-5-methoxy-6-methyl-7-chloro-1-indanone

By following substantially the procedure described in Example 9, Step C, using the following substances: 2'-chloro-3'-methyl-4'-methoxy-2-cyclopentylacrylophenone (36.3 g.) and sulfuric acid (200 ml.) there is obtained 30.7 g. (85%) of 2-cyclopentyl-5-methoxy-6-methyl-7-chloro-1-indanone which after recrystallization from hexane melts at 73°–74° C.

Elemental analysis for $C_{16}H_{19}ClO_2$: Calc.: C, 68.93; H, 6.87; Found: C, 69.08; H, 6.76.

Step D:
2-Cyclopentyl-2,6-dimethyl-5-methoxy-7-chloro-1-indanone

By following substantially the procedure described in Example 9, Step D, using the following substances: 2-cyclopentyl-5-methoxy-6-methyl-7-chloro-1-indanone (2.79 g., 0.01 mole), sodium hydride (0.264 g., 0.011 mole), 1,2-dimethoxyethane (100 ml.) and methyl iodide (3.11 ml., 0.05 mole) there is obtained 2.8 g. (96%) of 2-cyclopentyl-2,6-dimethyl-5-methoxy-7-chloro-1-indanone which melts at 48°–52° C. after purification by chromatography.

Elemental analysis for $C_{17}H_{21}ClO_2$: Calc.: C, 69.73; H, 7.23 Found: C, 69.68; H, 7.33

Step E:
2-Cyclopentyl-2,6-dimethyl-5-hydroxy-7-chloro-1-indanone

By following substantially the procedure described in Example 5, Step F, using the following substances: 2-cyclopentyl-2,6-dimethyl-5-methoxy-7-chloro-1-indanone (5.4 g., .0184 mole), aluminum chloride (7.36 g., 0.552 mole) and heptane (200 ml.), there is obtained 3.3 g. of 2-cyclopentyl-2,6-dimethyl-5-hydroxy-7-chloro-1-indanone, m.p. 175°–177° C. from ethanol-water.

Elemental analysis for $C_{16}H_{19}ClO_2$: Calc.: C, 68.93; H, 6.87; Found: C, 69.07; H, 6.71.

Step F:
(1-Oxo-2-cyclopentyl-2,6-dimethyl-7-chloro-5-indanyloxy)acetic Acid

By following substantially the procedure described in Example 9, Step F, using the following substances: 2-cyclopentyl-2,6-dimethyl-5-hydroxy-7-chloro-1-indanone (3.1 g., 0.011 mole), potassium carbonate (3.8 g., 0.0275 mole), ethyl bromoacetate (3.1 ml., .0275 mole) and DMF (50 ml.), there is obtained (1-oxo-2-cyclopentyl-2,6-dimethyl-7-chloro-5-indanyloxy)acetic acid yield 76 g., 117°–119° C. after triturating with hexane.

Elemental analysis for $C_{18}H_{21}ClO_4$: Calc.: C, 64.18; H, 6.29; Found: C, 64.22; H, 6.37.

EXAMPLE 18

(1-Oxo-2-cinnamyl-2-methyl-6,7-dichloro-5-indanyloxy)acetic Acid

Step A:
2-Cinnamyl-2-methyl-5-methoxy-6,7-dichloro-1-indanone

By following substantially the procedure described in Example 12, Step A, using the following substances: 2-methyl-5-methoxy-6,7-dichloro-1-indanone (2.5 g., 0.01 mole), tert-butylalcohol (65 ml.), benzene (60 ml.), potassium tert-butoxide (1.68 g., 0.015 mole) and cinnamyl bromide (2 g., 0.01 mole), there is obtained 3.4 g., (94%) of 2-cinnamyl-2-methyl-5-methoxy-6,7-dichloro-1-indanone which is used in the next step without purification.

Step B:
2-Cinnamyl-2-methyl-5-hydroxy-6,7-dichloro-1-indanone

By following substantially the procedure described in Example 7, Step B, using the following substances: 2-cinnamyl-2-methyl-5-methoxy-6,7-dichloro-1-indanone (3.4 g.) and pyridine hydrochloride (35 g.) there is obtained 2.3 g. (72%) of 2-cinnamyl-2-methyl-5-hydroxy-6,7-dichloro-1-indanone which after recrystallization from acetic acid-water melts at 201°–203° C.

Elemental analysis for $C_{19}H_{16}Cl_2O_3$: Calc.: C, 65.72; H, 4.64; Found: C, 65.62; H, 4.60.

Step C:
(1-Oxo-2-cinnamyl-2-methyl-6,7-dichloro-5-indanyloxy)acetic Acid

By following substantially the procedure described in Example 5, Step G, using the following substances: 2-cinnamyl-2-methyl-5-hydroxy-6,7-dichloro-1-indanone (2.6 g., 0.009 mole), ethyl bromoacetate (1.67 g., 0.010 mole), potassium carbonate (1.38 g., 0.010 mole) and DMF (30 ml.) there is obtained 1.6 g. (44%) of (1-oxo-2-cinnamyl-2-methyl-6,7-dichloro-5-indanyloxy)acetic acid which after recrystallization from benzene melts at 110°–120° C.

Elemental analsis for $C_{21}H_{18}Cl_2O_4$: Calc.: C, 62.24; H, 4.48; Found: C, 62.37; H, 4.53.

EXAMPLE 19

Ethyl (1-Oxo-2-isopropyl-2-methyl-3-bromo-6,7-dichloro-5-indanyloxy)acetate

Step A: Ethyl (1-oxo-2-isopropyl-2-methyl-6,7-dichloro-5-indanyloxy)acetate

To a solution of (1-oxo-2-isopropyl-2-methyl-6,7-dichloro-5-indanyloxy)acetic acid (8.0 g., 0.024 mole) in ethanol (50 ml.) is added boron trifluoride etherate (13 ml.). The reaction mixture is refluxed for ½ hour, treated with water and cooled to afford 7.5 g. (87%) of ethyl (1-oxo-2-isopropyl-2-methyl-6,7-dichloro-5-indanyloxy)acetate, m.p. 113° C.

Elemental analysis for $C_{17}H_{20}Cl_2O_4$: Calc.: C, 56.84; H, 5.61; Found: C, 56.82; H, 5.63.

Step B: Ethyl (1-oxo-2-isopropyl-2-methyl-3-bromo-6,7-dichloro-5-indanyloxy)acetate A solution of ethyl (1-oxo-2-isopropyl-2-methyl-6,7-dichloro-5-indanyloxy)acetate (3.6 g., 0.01 mole, N-bromosuccinimide (2.4 g., 0.0134 mole) and benzoyl peroxide (20 mg.) in carbon tetrachloride is refluxed 4 hours, cooled and filtered free of succinimide. The solvent is evaporated and the crude product is purified by column chromatography and then recrystallized from cyclohexane to afford substantially pure ethyl (1-oxo-2-isopropyl-2-methyl-3-bromo-6,7-dichloro-5-indanyloxy)acetate, m.p. 83°–85° C.

Elemental analysis for $C_{17}H_{19}BrCl_2O_4$: Calc.: C, 46.60; H, 4.37; Found: C, 46.80; H, 4.37.

EXAMPLE 20

(1-Oxo-2,2,3-trimethyl-6,7-dichloro-5-indanyloxy)acetic Acid

Step A: 2′,3′-Dichloro-4′-methoxy-2-methylbutyrophenone

By following the procedure described in Example 5, Step A, using as the reactants 2,3-dichloroanisole (100 g., 0.565 mole), 2-methylbutyryl chloride (.75 g., 0.62 mole), aluminum chloride (83 g., 0.62 mole) and methylene chloride (400 ml.), there is obtained 2′,3′-dichloro-4′-methoxy-2-methylbutyrophenone.

Step B: 2-Bromo-2-methyl-2′,3′-dichloro-4′-methoxybutyrophenone

By following the procedure described in Example 5, Step B, using as the reactants 2′,3′-dichloro-4′-methoxy-2-methylbutyrophenone (26 g., 0.10 mole), acetic acid (75 ml.) and bromine (16 g., 0.10 mole), there is obtained 2-bromo-2-methyl-2′,3′-dichloro-4′-methoxybutyrophenone.

Step C: 2-Ethylidene-2′,3′-dichloro-4′-methoxypropiophenone

By following the procedure described in Example 5, Step C, using as the reactants 2-bromo-2-methyl-2′,3′-dichloro-4′-methoxybutyrophenone (34 g., 0.1 mole), lithium bromide (17.4 g., 0.2 mole) and DMF (200 ml.), there is obtained 2-ethylidene-2′,3′-dichloro-4′-methoxypropiophenone.

Step D: 2,3-Dimethyl-5-methoxy-6,7-dichloro-1-indanone

By following the procedure described in Example 5, Step D, using as the reactants 2-ethylidene-2′,3′-dichloro4′-methoxypropiophenone (30 g.) and sulfuric acid (120 ml.), there is obtained 2,3-dimethyl-5-methoxy-6,7-dichloro-1-indanone.

Step E: 2,2,3-Trimethyl-5-methoxy-6,7-dichloro-1-indanone

By following the procedure described in Example 5, Step E, using as the reactants 2,3-dimethyl-5-methoxy-6,7-dichloro-1-indanone (13 g., 0.05 mole), sodium hydride (1.44 g., 0.06 mole), 1,2-dimethoxyethane (500 ml.) and methyl iodide (8 ml.), there is obtained 2,2,3-trimethyl-5-methoxy-6,7-dichloro-1-indanone.

Step F: 2,2,3-Trimethyl-5-hydroxy-6,7-dichloro-1-indanone

By following the procedure described in Example 7, Step B, using as the reactants 2,2,3-trimethyl-5-methoxy-6,7-dichloro-1-indanone (10 g.) and pyridine hydrochloride (100 g.), there is obtained 2,2,3-trimethyl-5-hydroxy-6,7-dichloro1-indanone.

Step G: (1-Oxo-2,2,3-trimethyl-6,7-dichloro-5-indanyloxy)acetic Acid

A mixture of 2,2,3-trimethyl-5-hydroxy-6,7-dichloro-1-indanone (6.1 g., 0.025 mole), iodoacetic acid (5.58 g., 0.03 mole) and potassium carbonate (4.14 g., 0.03 mole) in acetone (80 ml.) is refluxed for 20 hours. The acetone is evaporated and the residue is dissolved in water and acidified with hydrochloric acid. The (1-oxo-2,2,3-trimethyl-6,7-dichloro-5-indanyloxy)acetic acid which separates is filtered, rinsed with water and dried.

EXAMPLE 21

(1-Oxo-2-cyclopentyl-2,6,7-trimethyl-5-indanyloxy)acetic Acid

Step A: 2′,3′-Dimethyl-4′-methoxycyclopentylacetophenone

By following substantially the procedure described in Example 5, Step A, using the following substances: 2,3-dimethylanisole (73.9 g., 0.544 mole), cyclopentylacetyl chloride (87.6 g., 0.598 mole), aluminum chloride (80.0 g., 0.598 mole) and methylene chloride (500 ml.) there is obtained 114.4 g., (86%) of 2′,3′-dimethyl-4′-methoxycyclopentylacetophenone which distills at 150°–165° C./1 mm.

Elemental analysis for $C_{16}H_{22}O_2$: Calc.: C, 78.01; H, 9.00; Found: C, 78.20; H, 9.52.

Step B: 2′,3′-Dimethyl-4′-methoxy-2-cyclopentylacrylophenone

By following substantially the procedure described in Example 9, Step B, using the following substances: 2′,3′-dimethyl-4′-methoxycyclopentylacetophenone (71.5 g., 0.291 mole), paraformaldehyde (21.8 g.), dimethylamine hydrochloride (105 g.) and acetic acid (7.3 ml.), there is obtained 62 g. (82%) of 2′,3′-dimethyl-4′-methoxy-2-cyclopentylacrylophenone.

Step C: 2-Cyclopentyl-5-methoxy-6,7-dimethyl-1-indanone

By following substantially the same procedure described in Example 9, Step C, using the following substances: 2′,3′-dimethyl-4′-methoxy-2-cyclopentylacrylophenone (25.2 g.) and sulfuric acid (200 ml.) there is obtained 25.2 g. (100%) of 2-cyclopentyl-5-methoxy-6,7-dimethyl-1-indanone which after recrystallization from hexane melts at 69°–70° C.

Elemental analysis for $C_{17}H_{22}O_2$: Calc.: C, 79.03; H, 8.59; Found: C, 79.63; H, 8.87.

Step D: 2-Cyclopentyl-2,6,7-trimethyl-5-methoxy-1-indanone

By following substantially the pame procedure described in Example 11, Step A, using the following substances: 2-cyclopentyl-5-methoxy-6,7-dimethyl-1-indanone (2.58 g., 0.01 mole), tert-butanol (50 ml.), benzene (50 ml.), potassium tert-butoxide (1.68 g., 0.015 mole) and methyl iodide (3.12 ml., 0.05 mole) there is obtained 2-cyclopentyl-2,6,7-trimethyl-5-methoxy-1-indanone. The 2-cyclopentyl-2,6,7-trimethyl-5-methoxy-1-indanone is identified and characterized by its mass spectrum: m/c 272 (M+), 204 (base peak, m+- $C_5H_8$).

Step E:
2-Cyclopentyl-2,6,7-trimethyl-5-hydroxy-1-indanone

By following substantially the same procedure described in Example 7, Step B, using the following substances: 2-cyclopentyl-2,6,7-trimethyl-5-methoxy-1-indanone (10 g.) and pyridine hydrochloride (100 g.), there is obtained 2-cyclopentyl-2,6,7-trimethyl-5-hydroxy-1-indanone.

Step F:
(1-Oxo-2-cyclopentyl-2,6,7-trimethyl-5-indanyloxy)acetic Acid

By following substantially the same procedure described in Example 5, Step C, using the following substances: 2-cyclopentyl-2,6,7-trimethyl-5-hydroxy-1-indanone (6.45 g., 0.025 mole), potassium carbonate (7.0 g.), ethyl bromoacetate (8.3 g.) and DMF (65 ml.), there is obtained (1-oxo-2-cyclopentyl-2,6,7-trimethyl-5-indanyloxy)acetic acid.

By substituting for the 2,3-dimethylanisole of Example 21, Step A, an equimolar quantity of 2-chloro-3-methylanisole and by following substantially the procedures described in Steps A-F, there is obtained (1-oxo-2-cyclopentyl-2,7-dimethyl-6-chloro-5-indanyloxy)acetic acid.

EXAMPLE 22

α,α-Dimethyl-(1-Oxo-2-cyclopentyl-2-methyl-6,7-dichloro-5-indanyloxy)acetic Acid To a refluxing solution of 2-cyclopentyl-2-methyl-5-hydroxy-6,7-dichloro-1-indanone (15.5 g., 0.05 mole) in acetone (500 ml.) in an inert atmosphere is added solid sodium hydroxide (12.6 g., 0.25 mole). Chloroform (7.6 g., 0.69 mole) in acetone (50 ml.) is added dropwise during a 10-minute period. The reaction mixture is refluxed for 5 hours, then evaporated to dryness at reduced pressure. The residue is dissolved in water, filtered and acidified with hydrochloric acid and affording α,α-dimethyl-(1-oxo-2-cyclopentyl-2-methyl-6,7-dichloro-5-indanyloxy)acetic acid.

EXAMPLE 23

4-(1-Oxo-2-cyclopentyl-2-methyl-6,7-dichloro-5-indanyloxy)butyric Acid

By following the procedure described in Example 5, Step G, using as the reactants 2-cyclopentyl-2-methyl-5-hydroxy-6,7-dichloro-1-indanone (30.9 g., 0.1 mole), potassium carbonate (15.2 g., 0.11 mole), DMF (200 ml.), ethyl 4-bromobutyrate (23.5 g., 0.11 mole), water (200 ml.) and 10 N sodium hydroxide (40 ml.), there is obtained 4-(1-oxo-2-cyclopentyl-2-methyl-6,7-dichloro-5-indanyloxy)butyric acid.

EXAMPLE 24

3-(1-Oxo-2-cyclopentyl-2-methyl-6,7-dichloro-5-indanyloxy)propionic Acid

2-Cyclopentyl-2-methyl-5-hydroxy-6,7-dichloro-1-indanone (15.5 g., 0.05 mole) is dissolved in a 10% sodium hydroxide solution (50 ml.). The solution is heated to reflux and beta-propiolactone (36.0 g., 0.5 mole) is added at such a rate as to keep the reaction mixture refluxing. The reaction mixture is kept basic by the addition of 10% sodium hydroxide. The reaction mixture is cooled and acidified with dilute hydrochloric acid. The product is extracted with ether and extracted from the ether solution with a 5% solution of sodium bicarbonate. Acidification affords the desired product.

EXAMPLE 25

N-Ethyl (1-Oxo-2-isopropyl-2-methyl-6,7-dichloro-5-indanyloxy)acetamide

A solution of (1-oxo-2-isopropyl-2-methyl-6,7-dichloro-5-indanyloxy)acetic acid (0.6 g.) and thionyl chloride (0.3 ml.) in benzene (10 ml.) is refluxed for one hour. The solvent is distilled at reduced pressure and the residual oil is treated with benzene (20 ml.) and ethylamine (0.5 ml.). After one hour the reaction mixture is poured into water and extracted with ether which is washed with dilute hydrochloride acid and aqueous sodium bicarbonate. The ether solution is dried over magnesium sulfate and evaporated at reduced pressure affording N-ethyl (1-oxo-2-isopropyl-2-methyl-6,7-dichloro-5-indanyloxy)acetamide which melts at 146° C. after recrystallization from butyl chloride.

Elemental analysis for $C_{17}H_{21}Cl_2NO_3$: Calc.: C, 56.99; H, 5.91; N, 3.91; Found: C, 57.04; H, 6.04; N, 3.91.

EXAMPLE 26

(−) (1-Oxo-2-isopropyl-2-methyl-6,7-dichloro-5-indanyloxy)acetic Acid

To a solution of racemic (1-oxo-2-isopropyl-2-methyl-6,7-dichloro-5-indanyloxy)acetic acid (36.5 g., 0.11 mole) in absolute ethanol (200 ml.) is added a solution of 1-(−)-cinchonidine (32.5 g., 0.011 mole) in absolute ethanol (150 ml.). The salt which separates is recrystallized six times from acetonitrile dissolved in water and acidified with hydrochloric acid. The solution is extracted with ether, washed with water, dried over magnesium sulfate and the solvent evaporated at reduced pressure to afford (−) (1-oxo-2-isopropyl-2-methyl-6,7-dichloro-5-indanyloxy)acetic acid which melts at 145° C. after recrystallization from acetic acid-water.

$[\alpha]_D^{25} = -48.4°$ (C, 3, acetone)

Elemental analysis for $C_{15}H_{16}Cl_2O_4$ Calc.: C, 54.40; H, 4.87 Found: C, 53.95; H, 4.87

EXAMPLE 27

(+) (1-Oxo-2-isopropyl-2-methyl-6,7-dichloro-5-indanyloxy)acetic Acid

From the filtrates of Example 26 are isolated after treatment with aqueous acid partially resolved (+) (1-oxo-2-isopropyl-2-methyl-6,7-dichloro-5-indanyloxy)acetic acid 16.6 g., 0.050 mole) which is dissolved in acetonitrile (1.6 l.) and treated with cinchonine (14.7 g., 0.050 mole). The salt which separates is recrystallized five times from acetonitrile. The (+) (1-oxo-2-isopropyl-2-methyl-6,7-dichloro-5-indanyloxy)acetic acid is isolated as described in Example 26 and melts at 148° C. after recrystallization from acetic acid-water.

$[\alpha]_D^{25} = +48.4°$ (C, 3, acetone)

Elemental analysis for $C_{15}H_{16}Cl_2O_4$: Calc.: C, 54.40; H, 4.87 Found: C, 54.43; H, 4.98

EXAMPLE 28

(+)
(1-Oxo-2-cyclopentyl-2-methyl-6,7-dichloro-5-indanyloxy)acetic Acid

To a solution of racemic (1-oxo-2-cyclopentyl-2-methyl-6,7-dichloro-5-indanyloxy)acetic acid (66.51 g., 0.1862 mole) in absolute ethanol (500 ml.) is added a solution of 1-(−)-cinchonidine (54.81 g., 0.1862 mole) in absolute ethanol (500 ml.) and water (1 l.) is added. The salt which separates is recrystallized from 50% aqueous ethanol (six times). The (+) (1-oxo-2-cyclopentyl-2-methyl-6,7-dichloro-5-indanyloxy)acetic acid is isolated as described in Example 26 and melts at 70°–74° C.

$[\alpha]_D^{25} = +34°$ (C, 2, acetone)

Elemental analysis for $C_{17}H_{18}Cl_2O_4$: Calc.: C, 57.16; H, 5.08; Cl, 19.85 Found: C, 57.10; H, 5.41; Cl, 19.66

EXAMPLE 29

(−)
(1-Oxo-2-cyclopentyl-2-methyl-6,7-dichloro-5-indanyloxy)acetic Acid

From the filtrates of Example 28 there is obtained 8.3 g. (0.023 mole) of partially resolved (−)-(1-oxo--2-cyclopentyl-2-methyl-6,7-dichloro-5-indanyloxy)acetic acid which is combined with 1-(−)-α-methylbenzylamine (2.81 g., 0.023 mole) and the salt thus formed is recrystallized five times from 50% aqueous ethanol. The (−)-(1-oxo-2-cyclopentyl-2-methyl-6,7-dichloro-5-indanyloxy)acetic acid is isolated as described in Example 26 and melts at 70°–74° C.

$[\alpha]_D^{25} = -34°$ (C, 2, acetone)

Elemental analysis for $C_{17}H_{18}Cl_2O_4$: Calc.: C, 57.16; H, 5.08; Cl, 19.85 Found: C, 57.18; H, 5.36; Cl, 20.00

EXAMPLE 30

(1-Oxo-2-cyclopentyl-2-methyl-6,7-dichloro-5-indanylthio)acetic Acid

Step A:
2′,3′-Dichloro-4′-methylthio-2-cyclopentylacetophenone

2′,3′-Dichloro-4′-methylthio-2-cyclopentylacetophenone is prepared following substantially the same procedure described in Example 10, Step A, using the following substances: 2,3-dichlorothioanisole (63.1 g., 0.327 mole), methylene chloride (300 ml.), cyclopentylacetyl chloride (52.7 g., 0.367 mole) and aluminum chloride (48.0 g., 0.36 mole).

Step B:
2′,3′-Dichloro-4′-(2-cyclopentylacryloyl)thioanisole

2′,3′-Dichloro-4′-(2-cyclopentylacryloyl)thioanisole is prepared following substantially the same procedure described in Example 10, Step B, using the following substances: 2′,3′-dichloro-4′-methylthio-2-cyclopentylacetophenone (54.5 g., 0.18 mole), paraformaldehyde (21.6 g., 0.72 mole), concentrated sulfuric acid (9.65 g.) and dioxane (450 ml.).

Step C:
2-Cyclopentyl-5-methylthio-6,7-dichloro-1-indanone

2-Cyclopentyl-5-methylthio-6,7-dichloro-1-indanone is prepared following substantially the same procedure described in Example 10, Step C, using the following substances: 2′,3′-dichloro-4′-(2-cyclopentylacryloyl)thioanisole (10 g.) and concentrated sulfuric acid (50 ml.).

Step D:
2-Cyclopentyl-2-methyl-5-methylthio-6,7-dichloro-1-indanone

2-Cyclopentyl-2-methyl-5-methylthio-6,7-dichloro-1-indanone is prepared following substantially the same procedure described in Example 10, Step D, using the following substances: 2-cyclopentyl-5-methylthio-6,7-dichloro-1-indanone (7.9 g., 0.025 mole), 1,2-dimethoxyethane (200 ml.), sodium hydride (660 mg., 0.0275 mole) and methyl iodide (7.5 ml.).

Step E:
2-Cyclopentyl-2-methyl-5-mercapto-6,7-dichloro-1-indanone

To a stirred suspension of 2-cyclopentyl-2-methyl-5-methylthio-6,7-dichloro-1-indanone (3.59 g., 0.01 mole) in liquid ammonia (100 ml.) cooled in a dry-ice-acetone bath is added sodium (460 mg., 0.02 gr. atom) in small portions until a permanent blue color persists. Ammonium chloride (1.0 g.) is added, the excess ammonia is evaporated and the reaction mixture is dissolved in water, acidified and extracted with ether which is washed with water, dried over magnesium sulfate and evaporated at reduced pressure affording 2-cyclopentyl-2-methyl-5-mercapto-6,7-dichloro-1-indanone.

Step F:
(1-Oxo-2-cyclopentyl-2-methyl-6,7-dichloro-5-indanylthio)acetic Acid (1-Oxo-2-cyclopentyl-2-methyl-6,7-dichloro-5-indanylthio)acetic acid is prepared following substantially the same procedure described in Example 10, Step F, using the following substances: 2-cyclopentyl-2-methyl-5-mercapto-6,7-dichloro-1-indanone (3.47 g., 0.01 mole), DMF (40 ml.), potassium carbonate (2.78 g., 0.02 mole) and ethyl bromoacetate (2.9 g., 0.02 mole).

EXAMPLE 31

Preparation of
(1-oxo-2,2-dimethyl-3-phenyl-6,7-dichloro-5-indanyloxy)acetic acid

Step A: 2′,3′-Dichloro-4′-methoxypropiophenone

A stirred mixture of 2,3-dichloroanisole (177.0 g., 1.0 mole) and propionyl chloride (101.8 g., 1.1 mole) in methylene chloride (600 ml.) is cooled to 5° C. and treated with aluminum chloride (146.7 g., 1.1 mole) during a 1½ hour period. The reaction is allowed to warm to 25° C. and after 16 hours is poured into ice-water (2 l.) and concentrated hydrochloric acid (200 ml.). The organic phase is washed with 10% sodium hydroxide solution and saturated salt solution, and dried over magnesium sulfate. After evaporation of the solvent, the product is crystallized from hexane to give 124,5 g. (53%) of 2′,3′-dichloro-4′-methoxypropiophenone which melts at 51°–54° C.

Step B: 2,3-Dichloro-4-(2-benzylidenemethyl)anisole

To a mixture of 2′,3′-dichloro-4′-methoxypropiophenone (124.5 g., 0.53 mole) and benzaldehyde (54.5 ml., 0.53 mole) dissolved in ethanol (1 l.) is added dropwise 20% sodium hydroxide solution (117.0 ml., 0.59 mole). The product begins to precipitate after three quarters of the base has been added. After 2 hours at 25° C. the solid product is collected by suction filtration to give 163.2 g. (95%) of 2,3-dichloro-4-(2-benzylidenemethyl- )anisole which melts at 137.5°–139° C. After crystallization from ethanol.

Elemental Analysis for $C_{17}H_{14}Cl_2O_2$: Calc.: C, 63,57; H, 4.39. Found: C, 63.69; H, 4.49.

Step C:

2-Methyl-3-phenyl-5-methoxy-6,7-dichloro-1-indanone 2,3-Dichloro-4-(2-benzylidenemethyl)anisole (100 g., 0.32 mole) and trifluoroacetic acid (400 ml.) are heated at gentle reflux for 67 hours. The trifluoroacetic acid is removed, the oily residue triturated with ether to give 80.0 g. of 2-methyl-3-phenyl-5-methoxy-6,7-dichloro-1-indanone which on crystallization from benzene melts at 155°–157° C.

Elemental analysis for $C_{17}H_{14}Cl_2O_2$: Calc: C, 63.57; H, 4.39; Found: C, 63.17; H, 4.59.

Step D:

2,2-Dimethyl-3-phenyl-5-methoxy-6,7-dichloro-1-indanone

2-Methyl-3-phenyl-5-methoxy-6,7-dichloro-1-indanone (9.63 g., 0.03 mole) and methyl iodide (18.7 ml., 0.3 mole) dissolved in dimethylformamide (100 ml.) at 25° C. under nitrogen are treated portionwise with sodium methoxide (4.2 g., 0.036 mole) over a 45 minute period. Sodium iodide is filtered off, and the yellow filtrate is added to water (500 ml.) to precipitate 6.57 g. of 2,2-dimethyl-3-phenyl-5-methoxy-6,7-dichloro-1-indanone which melts at 146°–148° C. after crystallization from cyclohexane.

Elemental Analysis for $C_{18}H_{16}Cl_2O_2$: Calc.: C, 64.49; H, 4.81; Found: C, 64.56; H, 5.04.

Step E:

2,2-Dimethyl-3-phenyl-5-hydroxy-6,7-dichloro-1-indanone

A stirred mixture of 2,2-dimethyl-3-phenyl-5-methoxy-6,7-dichloro-1-indanone (6.5 g., 0.02 mole) and pyridine hydrochloride (60 g.) is heated at 180° C. for 2 hours, then poured into water (800 ml.). The 2,2-dimethyl-3-phenyl-5-hydroxy-6,7-dichloro-1-indanone which separate (5.10 g.) melts at 259°–262° C. after recrystallization from ethanol water, 2:1.

Elemental Analysis for $C_{17}H_{14}Cl_2O_2$: Calc.: C, 63.57; H, 4.39; Found: C, 63.09; H, 4.52.

Step F:

(1-Oxo-2,2-dimethyl-3-phenyl-6,7-di-chloro-5-indanyloxy)acetic acid

A stirred mixture of 2,2-dimethyl-3-phenyl-5-hydroxy-6,7-dichloro-1-indanone (5.0 g., 0.0156 mole) potassium carbonate (4.32 g., 0.0312 mole) and ethyl bromoacetate (5.22 g., 0.0312 mole) in dimethylformamide (60 ml.) is warmed at 55°–60° C. for 3 hours, then treated with potassium hydroxide (2.29 g., 0.0343 mole) dissolved in a minimum amount of water in methanol (60 ml.) and heated on a steam bath for 3 hours. The reaction mixture is poured into water (600 ml.) and acidified with 6N hydrochloric acid to precipitate the product which on trituration with hexane and crystallization from acetic acid:water, 1:1, gives 2.52 g. of (1-oxo-2,2-dimethyl-3-phenyl-6,7-dichloro-5-indanyloxy) acetic acid which melts at 163°–164.5° C.

Elemental analysis for $C_{19}H_{16}Cl_2O_4$: Calc.: C, 60.17; H, 4.25; Cl, 18.70 Found: C, 59.57; H, 3.91; Cl, 18.81

EXAMPLE 32

Preparation of (1-Oxo-2,2,3-trimethyl-3-phenyl-6,7-dichloro-5-indanyloxy)acetic acid Step A:

2,2,3-Trimethyl-3-phenyl-5-methoxy-6,7-dichloro-1-indanone

2-Methyl-3-phenyl-5-methoxy-6,7-dichloro-1-indanone (9.63 g., 0.03 mole) and methyl iodide (18.7 ml., 0.3 mole) dissolved in dimethylformamide (100 ml.) under nitrogen at 25° C. are treated with potassium tert-butoxide (6.72 g., 0.06 mole) portionwise with intermittent cooling in an ice-water bath over a 5 hour period. After exhaustive alkylation, i.e., after the addition of methyl iodide (3 × 20 ml.) followed by potassium tert-butoxide (5 g.), this procedure repeated until the addition of the base gives no green color, acidified with 6N hydrochloric acid to precipitate the product which on trituration with hexane and crystallization from acetic acid: water, 1:1, gives 3.49 g. of (1-oxo-2,2,3-trimethyl-3-phenyl-6,7-dichloro-5-indanyloxy)acetic acid which melts at 189°–190° C.

Elemental analysis for $C_{20}H_{18}Cl_2O_4$: Calc.: C, 61.08; H, 4.61; Found: C, 61.21; H, 4.69.

EXAMPLE 33

Preparation of [1-Oxo-2-(3-hydroxybutyl)-2-isopropyl-6,7-dichloro-5-indanyloxy]acetic acid Step A:

[1-Oxo-2-isopropyl-2-(3-oxobutyl)-6,7-dichloro-5-indanyloxy]acetic acid

A stirred solution of (1-oxo-2-isopropyl-6,7-dichloro-5-indanyloxy)acetic acid (3.17 g., 0.01 mole) and sodium methoxide (3.2 g., 0.05 mole) in methanol (100 ml.) and benzene (100 ml.) in an inert atmosphere is cooled to 0° C. and treated with methyl vinyl ketone (2.0 g., 0.029 mole) in methanol (10 ml.) during a ½ hour period then stirred 72 hours at 25° C. The reaction mixture is acidified with acetic acid, evaporated to dryness, extracted with chloroform, washed with water, dried over magnesium sulfate and evaporated to dryness affording [1-oxo-2-isopropyl-2-(3-oxobutyl)-6,7-dichloro-5-indanyloxy]acetic acid which melts at 125°–128° C. after recrystallization from methanol.

Elemental analysis for $C_{18}H_{20}Cl_2O_5$: Calc.: C, 54.43; H, 5.77; Found: C, 54.48; H, 5.85.

Step B:

[1-Oxo-2-(3-hydroxybutyl)-2-isopropyl-6,7-dichloro-5-indanyloxy]acetic acid

A stirred suspension of [1-oxo-2-isopropyl-2-(3-oxobutyl)-6,7-dichloro-5-indanyloxy]acetic acid (2.0 g., 0.0052 mole) in water (50 ml.) is cooled to 5° C. and treated over a ½ hour period with a solution of potassium borohydride (0.6 g., 0.11 mole). The reaction is stirred at 10°–15° C. for ½ hour then acidified with dilute aqueous hydrochloric acid affording [1-oxo-2-(3-hydroxybutyl)-2-isopropyl-6,7-dichloro-5-indanyloxy]-acetic acid as a white solid which is filtered, rinsed with water and dried.

Elemental analysis for $C_{18}H_{22}Cl_2O_5$: Calc.: C, 55.54; H, 5.70; Cl, 18.22; Found: C, 55.54; H, 6.21; Cl, 18.17.

EXAMPLE 34

Preparation of
1-oxo-2-(hydroxycyclopentyl)-2-methyl-6,7-dichloro-5-indanyloxyacetic acid 8 Ml. of sterile hydroxylated production media is added to a slant of fungal microorganism. The hydroxylated product medium is prepared by combining 50 g./l. cerelose
20 g./l. edamine
5 ml/l. corn steep liquor and bringing this total solution to a pH of 6.5 with sodium hydroxide. 1Liter of distilled tap water is added and the hydroxylated product media is then heated to 121° C. in an autoclave. Surface growth is scraped off and transferred to a 250 ml. flask with 32 ml. of sterile medium. The mixture is shaken for one hour to dispense the cells. After shaking, an additional 22 ml. of medium is added and the mixture is again shaken to give a total volume of about 62 ml. Each of seven 2 liter flasks containing 22 ml. of medium are inoculated with 8 ml. of cell suspension. The flasks are incubated at 28° C. at 220 revolutions per minute for 48 hours. To each flask is added 1.6 ml. of methyl alcohol solution of 100 mg/ml of 1-oxo-2-cyclopentyl-2-methyl-6,7-dichloro-5-indanyloxyacetic acid. Incubation was terminated 48 hours after the addition of the starting material above by the addition of 8 ml. of 85% phosphoric acid to each flask. One drop of polyglycol P-2000 is added to each flask and the solution passed through sintered glass filter to separate the medium from the cells.

To the combined spent medium of each flask was added 1000 ml of ethyl acetate and the entire mixture shaken for 2 minutes in a separatory funnel. The lower phase is drawn off the emulsion and upper phase passed through a sintered glass filter to break the emulsion. The resulting upper phase was separated from the remaining lower phase and blown to dryness with a stream of nitrogen. Thin layer chromatography showed about 150 mg. of starting material and 750 mg. of 1-oxo-2-(hydroxycyclopentyl)-2-methyl-6,7-dichloro-5-indanyloxyacetic acid.

EXAMPLE 35

(1-Oxo-2-cyclopentyl-2-methyl-6,7-dichloro-5-indanyloxy)acetic anhydride

A stirred solution of (1-oxo-2-cyclopentyl-2-methyl-6,7-dichloro-5-indanyloxy)acetic acid (14.3 g., 0.04 mole) in methylene chloride (100 ml.) is treated with a solution of dicyclohexyl-carbodiimide (4.12 g.) in methylene chloride (50 ml.). After 1 hour the solvent is evaporated and the residue treated with ether (100 ml.). The dicyclohexylurea is filtered and the ether evaporated at reduced pressure affording (1-oxo-2-cyclopentyl-2-methyl-6,7-dichloro-5-indanyloxy)acetic anhydride as a viscous yellow oil.

EXAMPLE 36

Preparation of
N-Amidino-(1-oxo-2-cyclopentyl-2-methyl-6,7-dichloro-5-indanyloxy)acetamide Step A:
(1-Oxo-2-cyclopentyl-2-methyl-6,7-dichloro-5-indanyloxy)acetyl chloride A solution of (1-oxo-2-cyclopentyl-2-methyl-6,7-dichloro-5-indanyloxy)acetic acid (3.57 g., 0.01 mole) and thionyl chloride (2.38 g., 0.02 mole) in benzene (50 ml.) is refluxed for 1 hour. The excess thionyl chloride and benzene are evaporated at reduced pressure as is a subsequent 50 ml. portion of benzene affording (1-oxo-2-cyclopentyl-2-methyl-6,7-dichloro-5-indanyloxy)acetyl chloride as a yellow oil which is used in step B without further purification.

Step B:
N-Amidino-(1-oxo-2-cyclopentyl-2-methyl-6,7-dichloro-5-indanyloxy)acetamide A solution of guanidine hydrochloride (4.8 g., 0.05 mole) in methanol (50 ml.) is treated with sodium methoxide (2.7 g., 0.05 mole), stirred for five minutes, filtered free of sodium chloride, evaporated at reduced pressure to a volume of 10 ml. and treated with the product of step A. After one-half hour the reaction mixture is treated with water affording N-amidino-(1-oxo-2-cyclopentyl-2-methyl-6,7-dichloro-5-indanyloxy)acetamide which melts at 216° C.

Elemental analysis for $C_{18}H_{21}Cl_2N_3O_2$: Calc.: C, 54.28; H, 5.31; N, 10.55; Found: C, 54.47; H, 5.66; N, 10.33.

EXAMPLE 37

Preparation of Methyl
(1-oxo-2-cyclopentyl-2-methyl-6,7-dichloro-5-indanyloxy)acetate A solution of 1-oxo-2-cyclopentyl-2-methyl-6,7-dichloro-5-indanyloxy)acetic acid (357 mg., 1 mmole) in ether (5 ml.) is treated with an ethereal solution of diazomethane until a yellow color persists. Evaporation of the ether and excess diazomethane affords methyl (1-oxo-2-cyclopentyl-2-methyl-6,7-dichloro-5-indanyloxy)-acetate.

EXAMPLE 38

(1-Oxo-2-ethyl-2-methyl-3-phenyl-6,7-dichloro-5-indanyloxy)-acetic Acid

Step A:
2',3'-Dichloro-4'-methoxybutyrophenone

A solution of 2',3'-dichloro-4'-hydroxybutyrophenone (57 g., 0.248 mole) in methanol (400 ml.) is heated to reflux. A solution of sodium hydroxide (40 g. in 100 ml. of water) and dimethyl sulfate are added alternately in small portions over ½ hour to maintain the alkalinity of the reaction mixture. On cooling, a solid separates and is recrystallized from hexane to afford 50.2 g. of 2',3'-dichloro-4'-methoxybutyrophenone, m.p. 42°–44° C.

Elemental analysis for $C_{11}H_{12}Cl_2O_2$: Calc.: C, 53.46; H, 4.89 Found: C, 53.71; H, 4.93

Step B:
2,3-Dichloro-4-(2-benzylidenebutyryl) anisole

To a mixture of benzaldehyde (19.4 g., 0.183 mole) and 2',3'-dichloro-4'-methoxybutyrophenone (42.2 g., 0.183 mole) in absolute ethanol (350 ml.) a 20% sodium hydroxide solution (35.9 ml.) is added dropwise with stirring. The mixture is stirred for 22 hours. The white solid product that separates is collected and air dried. Yield 55.6 g. (91%), m.p. 127°–130° C.

Elemental analysis for $C_{18}H_{16}Cl_2O_2$: Calc.: C, 64.49; H, 4.81 Found: C, 64.39; H, 4.79

Step C:
2-Ethyl-3-phenyl-6,7-dichloro-5-methoxy 1-indanone 2,3-Dichloro-4-(2-benzylidenebutyryl)anisole (111.0 g., 0.331 mole) and trifluoroacetic acid (350 ml.) are heated at gentle reflux for 70 hours. The trifluoroacetic acid is removed, the oily residue triturated with ether to give 88.1 g. (80%) of 2-ethyl-3-phenyl-6,7-dichloro-5-methoxy-1-indanone which on crystallization from benzene melts at 141°–143° C.

Elemental analysis for $C_{18}H_{16}Cl_2O_2$: Calc.: C, 64.49; H, 4.81 Found: C, 64.48; H, 4.87

Step D:
2-Ethyl-2-methyl-3-phenyl-6,7-dichloro-5-methoxy-1-indanone

2-Ethyl-3-phenyl-6,7-dichloro-5-methoxy-1-indanone (10.05 g., 0.03 mole) and methyl iodide (12.5 ml., 0.2 mole) dissolved in dimethylformamide (100 ml.)-benzene (100 ml.) at 0° C. under nitrogen are treated portionwise with sodium methoxide (3.54 g., 0.033 mole) over a 30 minute period. The reaction mixture is stirred in an ice-water bath for one hour, then poured into water (500 ml.), extracted with benzene, the organic layer separated, dried over anhydrous magnesium sulfate, filtered and concentrated to dryness to give an oily residue which on trituration with hexane gives 7.64 g. (71%) of 2-ethyl-2-methyl-3-phenyl-6,7-dichloro-5-methoxy-1-indanone which melts at 132° C. on crystallization from cyclohexane.

Elemental analysis for $C_{19}H_{18}Cl_2O_2$: Calc.: C, 65.34; H, 5.19; Found: C, 66.05; H, 5.36.

Step E:
2-Ethyl-2-methyl-3-phenyl-6,7-dichloro-5-hydroxy-1-indanone

A stirred mixture of 2-ethyl-2-methyl-3-phenyl-6,7-dichloro-5-methoxy-1-indanone (7.0 g., 0.02 mole) and pyridine hydrochloride (70 g.) is heated at 180° C. for two hours, then poured into water (800 ml.). The 2-ethyl-2-methyl-3-phenyl-6,7-dichloro-5-hydroxy-1-indanone which separates (6.64 g.) melts at 248° C. after recrystallization from ethanol: water, 2:1.

Elemental analysis for $C_{18}H_{16}Cl_2O_2$: Calc.: C, 64.49; H, 4.81; Found: C, 64.64; H, 4.83.

Step F:
(1-Oxo-2-ethyl-2-methyl-3-phenyl-6,7-dichloro-5-indanyloxy)acetic Acid A stirred mixture of 2-ethyl-2-methyl-3-phenyl-6,7-dichloro-5-hydroxyl-1-indanone (6.24 g., 0.0186 mole), potassium carbonate (5.15 g., 0.0372 mole) and ethyl bromoacetate (6.22 g., 0.0372 mole) in dimethylformamide (60 ml.) is warmed at 55°–60° C. for 3 hours, then treated with water (60 ml.) and 10N sodium hydroxide solution (5 ml., 0.05 mole) and heated at 80° C. for 1 hour. The reaction mixture is added slowly to water (800 ml.)-6N hydrochloric acid (20 ml.) to precipitate (1-oxo-2-ethyl-2-methyl-3-phenyl-6,7-dichloro-5-indanyloxy)acetic acid (3.7 g.) which melts at 192° C. on crystallization from Elemental analysis for $C_{20}H_{18}Cl_2O_4$: Calc.: C, 61.08; H, 4.61; Found: C, 61.33; H, 4.65.

EXAMPLE 39

5-(1-Oxo-2-cyclopentyl-2-methyl-6,7-dichloro-5-indanyloxy methyl)tetrazole

Step A:
(1-Oxo-2-cyclopentyl-2-methyl-6,7-dichloro-5-indanyloxy)acetonitrile By following substantially the same procedure described in Example 38, Step A, using the following substances: 2-cyclopentyl-2-methyl-5-hydroxy-6,7-dichloro-1-indanone (8.98 g., 0.03 mole), potassium carbonate (4.15 g.), chloroacetonitrile (2.26 g., 0.03 mole), potassium iodide (0.495 g.) and acetone (150 ml.) there is obtained 7.40 g. (73%) of (1-oxo-2-cyclopentyl-2-methyl-6,7-dichloro-5-indanyloxy)-acetonitrile which after recrystallization from benzenecyclohexane (1:10) melts at 130°–131° C.

Elemental analysis for $C_{17}H_{17}Cl_2NO_2$: Calc.: C, 60.36; H, 5.07; N, 4.14 Found: C, 60.62; H, 5.08; N, 3.88

Step B:
5-(1-Oxo-2-cylopentyl-2-methyl-6,7-dichloro-5-indanyloxymethyl)tetrazole By following substantially the same procedure described in Example 38, Step B, using the following substances: (1-oxo-2-cyclopentyl-2-methyl-6,7-dichloro-5-indanyloxy)-acetonitrile (7.20 g., 0.0213 mole), dimethylformamide (40 ml.), sodium azide (1.69 g., 0.0259 mole) and ammonium chloride (1.39 g., 0.0259 mole) there is obtained 4.74 g. of 5-(1-oxo-2-cyclopentyl-2-methyl-6,7-dichloro-5-indanyloxymethyl)tetrazole which melts at 218°–219° C. after recrystallization from ethanol.

Elemental analysis for $C_{17}H_{18}Cl_2N_4O_2$: Calc.: C, 53.55 H, 4.76; N, 14.70 Found: C, 53.63; H, 4.88; N, 14.77

EXAMPLE 40

5-[1'-Oxo-6',7'-dichlorospiro(cyclohexane-1,2'-indan)-5'-yloxymethyl]tetrazole

Step A:
[1'-Oxo-6',7'-dichlorospiro(cyclohexane-1,2'-indan)-5'-yloxy]acetonitrile The title compound is prepared following substantially the same procedure described in Example 38, Step A, using the following substances: 5'-hydroxy-6',7'-dichlorospiro(cyclohexane-1,2'-indanone) (8.55 g.), potassium carbonate (4.15 g.), chloroacetonitrile (2.4 g.), potassium iodide (0.5 g.) and acetone (150 ml.). This procedure affords 8.0 g. (82%) of [1'-oxo-6',7'-dichlorospiro(cyclohexane-1,2'-indan)-5'-yloxy]-acetonitrile which after recrystallization from butyl chloride melts at 165°–167° C.

Elemental analysis for $C_{16}H_{15}Cl_2NO_2$: Calc.: C, 59.27; H, 4.66; N, 4.32 Found: C, 59.60; H, 4.78; N, 4.34

Step B:
5-[1'-Oxo-6',7'-dichlorospiro(cyclohexane-1,2'-indan)-5'-yloxymethyl]tetrazole The title compound is prepared following substantially the same procedure described in Example 38, Step B, using the following substances: 5'-hydroxy-6',7'-dichlorospiro-(cyclopentane-1,2'-indanone) (8.4 g.), potassium carbonate (4.15 g.), chloroacetonitrile (2.4 g.), potassium iodide (0.5 g.) and acetone (150 ml.). This procedure affords 9.0 g. of [1'-oxo-6',7'-dichlorospiro(-cyclopentane-1,2'-indan)-5'-yloxy]acetonitrile which after recrystallization from butyl chloride melts at 153° C.

Elemental analysis for $C_{16}H_{16}Cl_2N_4O_2$: Calc.: C, 52.33; H, 4.39; N, 15.26 Found: C, 52.66; H, 4.49; N, 14.85

EXAMPLE 41

5-[1'-Oxo-6',7'-dichlorospiro(cyclopentane-1,2'-indan)-5'-yloxymethyl]tetrazole

Step A:
[1'-Oxo-6',7'-dichlorospiro(cyclopentane-1,2'-indan)-5'-yloxy]acetonitrile The title compound is prepared following substantially the same procedure described in Example 38, Step B, using the following substances: 5'-hydroxy-6',7'-dichlorospiro(cyclopentane-1,2'-indanone) (8.4 g.), potassium carbonate (4.15 g.), chloroacetonitrile (2.4 g.), potassium iodide (0.5 g.) and acetone (150 ml.). This procedure affords 2.0 g. of [1'-oxo-6',7'-dichlorospiro(cyclopentane-1,2'-indan)-5'-yloxy]acetonitrile which after recrystallization from butyl chloride melts at 153° C.

Elemental analysis for $C_{15}H_{13}Cl_2NO_2$: Calc.: C, 58.08; H, 4.22; N, 4.52 Found: C, 58.27; H, 4.22; N, 4.35

Step B:
5-[1'-Oxo-6',7'-dichlorspiro(cyclopentane-1,2'-indan)-5'-yloxymethyl]tetrazole The title compound is prepared following substantially the same procedure described in Example 38, Step B, using the following substances: [1'-oxo-6',7'-dichlorospiro(cyclopentane-1,2'-indan)-5'-yloxy]acetonitrile (5.3 g.), sodium azide (1.44 g.), ammonium chloride (1.14 g.) and dimethylformamide (35 ml.). This procedure affords 5.0 g. (83%) of 5-[1'-oxo-6',7'-dichlorospiro(cyclopentane-1,2'-indan)5'-yloxymethyl]tetrazole which after recrystallization from acetonitrile melts at 191° C.

Elemental analysis for $C_{15}H_{14}Cl_2N_4O_2$: Calc.: C, 51.01, H, 3.99; N, 15.86 Found: C, 51.27; H, 3.99; N, 16.22

EXAMPLE 42

Preparation of (1-Oxo-2-isopropyl-2-tert.-butoxymethyl-6,7-dichloro-5-indanyloxy)acetic Acid A solution of (1-oxo-2-hydroxymethyl-2-isopropyl-6,7-dichloro-5-indanyloxy)acetic acid (4.0 g., 0.012 mole), isobutylene (6 ml.), chloroform (20 ml.) and concentrated sulfuric acid (0.1 ml.) is sealed from the atmosphere and stirred at 25° C. for two weeks. After this time, the reaction mixture is poured into saturated aqueous sodium bicarbonate. The chloroform layer is separated, washed with water, dried and the chloroform distilled at reduced pressure affording tert.-butyl-(1-oxo-2-isopropyl-2-tert.-butoxymethyl-6,7-dichloro-5-indanyloxy)acetate which is hydrolyzed in a refluxing solution of methanolic potassium hydroxide. Acidification of the hydrolysis solution affords (1-oxo-2-isopropyl-2-tert.-butoxymethyl-6,7-dichloro-5-indanyloxy)-acetic acid which melts at 148°–149° C. after recrystallization from acetic acid-water.

Elemental analysis for $C_{19}H_{24}Cl_2O_5$:Calc.: C, 56.59; H, 6.00 Found: C, 57.01; H, 6.17

The novel compounds of this invention are diuretic and saluretic agents. In addition, these compounds are also able to maintain the uric acid concentration in the blood at pretreatment levels or even cause a decrease in uric acid concentration.

Also the compounds of this invention are antihydpertensive agents. Generally, we have found that an aryl or substituted aryl group but particularly a phenyl group at the 3-position of the compounds of Formula I will increase the uricosuric acitivity of the compounds when compared to the diuretic or saluretic activities.

The compounds of this invention can be administered in a wide variety of therapeutic dosages in conventional vehicles as, for example, by oral administration in the form of a tablet or by intravenous injection. Also, the daily dosage of the products may be varied over a wide range as, for example, in the form of scored tablets containing 5, 10, 25, 50, 100, 150, 250 and 500 milligrams of the active ingredient for the symptomatic adjustment of the dosage to the patient to be treated. These dosages are well below the toxic or lethal dose of the products.

A suitable unit dosage form of the products of this invention can be administered by mixing 50 milligrams of a 1-oxo-2,2-disubstituted-5-indanyloxyalkanoic acid (I) or a suitable salt, ester or amide derivative thereof, with 149 mg. of lactose and 1 mg. of magnesium stearate and placing the 200 mg. mixture into a No. 1 gelatin capsule. Similarly, by employing more of the active ingredient and less lactose, other dosage forms can be put up in No. 1 gelatin capsules and should it be necessary to mix more than 200 mg. of ingredients together, larger capsules may be employed. Compressed tablets, pills, or other desired unit dosages can be prepared to incorporate the compounds of this invention by conventional methods, and, if desired, can be made up as elixirs or as injectable solutions by methods well known to pharmacists. An effective amount of the drug is ordinarily supplied at a dosage level of from about 0.1 mg. to about 50 mg./kg. of body weight. Preferably the range is from about 1 mg. to 7 mg./kg. of body weight.

It is also within the scope of this invention to combine two or more of the compounds of this invention in a unit dosage form or to combine one or more of the compounds of this invention with other known diuretics and saluretics or with other desired therapeutic and/or nutritive agents in dosage unit form. For example, the compounds of this invention can be combined with anticaluretic-diuretic or with anti-hypertensive compounds, and particularly with an agent such as reserpine. Also a combination or mixture of different indanones of Formula I with each other can be advantageous particularly where one compound has greater diuretic activity and the other has greater uricosuric activity.

The following example is included to illustrate the preparation of a representative dosage form:

EXAMPLE 43

Dry-filled capsules containing 50 mg. of active ingredient per capsule

|  | Per Capsule |
|---|---|
| (1-Oxo-2-cyclopentyl-2-methyl-6,7-dichloro-5-indanyloxy)acetic acid | 50 mg. |
| Lactose | 149 mg. |
| Magnesium Stearate | 1 mg. |
| Capsule (Size No. 1) | 200 mg. |

The (1-oxo-2-cyclopentyl-2-methyl-6,7-dichloro-5-indanyloxy)acetic acid is reduced to a No. 60 powder and then lactose and magnesium stearate are passed through a No. 60 bolting cloth onto the powder and the combined ingredients admixed for 10 minutes and then filled into a No. 1 dry gelatin capsule.

Similar dry-filled capsules can be prepared by replacing the active ingredient of the above example by any of the other novel compounds of this invention.

EXAMPLE 44

Parenteral Solution of Sodium (1-Oxo-2-cyclopentyl-2-methyl-6,7-dichloro-5-indanyloxy)acetate 100 Mg. of (1-oxo-2-cyclopentyl-2-methyl-6,7-dichloro-5-indanyloxy)acetic acid are dissolved in 3 ml. of 0.1 N-sodium hydrogen carbonate solution. The solution is made up to 10 ml. with water and sterilized.

EXAMPLE 45

Dry-filled capsule containing 50 mg. of active ingredient and 5 mg. of N-amidino-(3,5-diamino-6-chloropyrazine)-2-carboxamide per capsule

|  | Per capsule |
|---|---|
| (1-oxo-2-cyclopentyl-2-methyl-6,7-dichloro-5-indanyloxy)acetic acid | 50 mg. |
| N-amidino-(3,5-diamino-6-chloropyrazine)-2-carboxamide | 5 mg. |
| lactose | 144 mg. |
| magnesium stearate | 1 mg. |
| capsule (size No. 1) | 200 mg. |

The (1-oxo-2-cyclopentyl-2-methyl-6,7-dichloro-5-indanyloxy)acetic acid and N-amidino-(3,5-diamino-6-chloropyrazine)-2-carboxamide are united and reduced to a No. 60 powder and then lactose and magnesium stearate are passed through a No. 60 bolting cloth onto the powder and the combined ingredients admixed for ten minutes and then filled into a No. 1 dry gelatin capsule.

EXAMPLE 46

Dry-filled capsules containing 50 mg. of active ingredient and 0.125 mg. of reserpine per capsule

|  | Per capsule |
|---|---|
| (1-oxo-2-cyclopentyl-2-methyl-6,7-dichloro-5-indanyloxy)acetic acid | 50 mg. |
| reserpine | 0.125 mg. |
| lactose | 148.875 mg. |
| magnesium stearate | 1 mg. |
| capsule (size No. 1) | 200 mg. |

The (1-oxo-2-cyclopentyl-2-methyl-6,7-dichloro-5-indanyloxy)acetic acid and reserpine are united and reduced to a No. 60 powder and then lactose and magnesium stearate are passed through a No. 60 bolting cloth onto the powder and the combined ingredients are admixed for ten minutes and then filled into a No. 1 dry gelatin capsule.

Similar dry-filled capsules can be prepared by replacing the indanyloxyacetic acid ingredient of the above example by any of the compounds of this invention.

EXAMPLE 47

Dry-filled capsules containing 25 mg. of active ingredient and 250 mg. of levo-3-(3,4-dihydroxyphenyl)-2-methylalanine

|  | Per Capsule |
|---|---|
| (1-Oxo-2-cyclopentyl-2-methyl-6,7-dichloro-5-indanyloxy)acetic acid | 25 mg. |
| Levo-3-(3,4-dihydroxyphenyl)-2-methylalanine | 250 mg. |
| Lactose | 124 mg. |
| Magnesium Stearate | 1 mg. |
| Capsule (Size No. 0) | 400 mg. |

The (1-oxo-2-cyclopentyl-2-methyl-6,7-dichloro-5-indanyloxy)acetic acid and levo-3-(3,4-dihydroxyphenyl)-2-alanine are united and reduced to a No. 60 powder and then lactose and magnesium stearate are passed through a No. 60 bolting cloth onto the powder and the combined ingredients admixed for 10 minutes and then filled into a No. 0 dry gelatin capsule.

It will be apparent from the foregoing description that the 1-oxo-2,2-disubstituted-5-indanyloxyalkanoic acid products (I) of this invention constitute a valuable class of compounds which have not been prepared heretofore. One skilled in the art will also appreciate that the processes disclosed in the above examples are merely illustrative and are capable of a wide variation and modification without departing from the spirit of this invention.

What is claimed is:

1. A compound of the formula

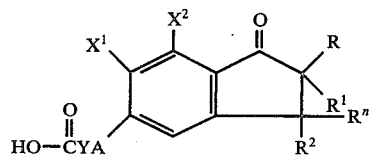

wherein
A is oxygen or sulfur
R and $R^1$ are joined together with the carbon atom to which they are attached to form cycloalkyl or hydroxy cycloalkyl wherein the cycloalkyl radical contains from 3 to 7 carbon atoms;
$R^2$ is hydrogen, halo, lower alkyl, aryl or substituted aryl;
$R^n$ is hydrogen or methyl;
$X^1$ is hydrogen, methyl or halo; and
$X^2$ is methyl or halo; or
$X^1$ and $X^2$ are joined to form a hydrocarbylene chain containing 3 to 4 carbon atoms; and
Y is alkylene or haloalkylene containing a maximum of 4 carbon atoms, and the non-toxic pharmacologically acceptable salt, amide, anhydride and ester derivatives thereof.

2. A compound of the formula

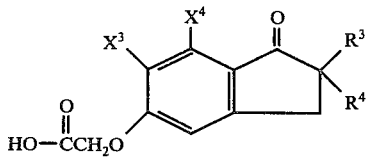

wherein
- R³ and R⁴ are joined together with the carbon atoms to which they are attached to form a cycloalkyl containing from 5 to 6 nuclear carbon atoms;
- X³ and X⁴ are the same or different radicals selected from methyl or chloro, and the non-toxic, pharmacologically acceptable salt derivatives thereof.

3. A compound according to claim 2 wherein R³ and R⁴ to form cyclopentane ring and X³ and X⁴ are chloro; which is [1'-oxo-6',7'-dichlorospiro(cyclopentane-1,2'-indan)-5'-yloxy]acetic acid.

4. A compound according to claim 2 wherein R³ and R⁴ form cyclohexane ring and X³ and X⁴ are chloro; which is [1'-oxo-6',7'-dichlorospiro(cyclohexane-1,2'-indan)-5'-yloxy]acetic acid.

5. A compound according to claim 1 wherein R and R¹ taken together are propylene; X¹ and X² are chloro; A is oxygen, Y is methylene and R" is hydrogen; which is [1'-oxo-2-methyl-6',7'-dichlorospiro(cyclopropane-1,2'-indan)-5'-yloxy]acetic acid.

6. A pharmaceutical composition useful in the treatment of edema and hypertension which also maintains uric acid at pretreatment levels or causes a decrease in uric acid levels which comprises 10 mg. to 500 mg. of a compound of the formula:

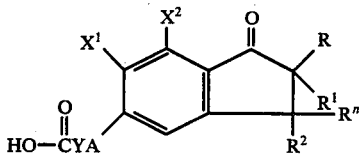

wherein
- A is oxygen or sulfur;
- R and R¹ are joined to form a cycloalkyl or hydroxy cycloalkyl wherein the cycloalkyl radical contains from 3 to 7 carbon atoms;
- R² is hydrogen, halo, aryl, substituted aryl or lower alkyl;
- R" is methyl or hydrogen;
- X¹ is hydrogen, methyl or halo; and
- X² is methyl or halo; or
- X¹ and X² are joined to form a hydrocarbylene chain containing 3 to 4 carbon atoms and
- Y is alkylene or haloalkylene containing a maximum of 4 carbon atoms, and the non-toxic, pharmacologically acceptable salt, amide, anhydride and ester derivatives and a pharmaceutically acceptable carrier.

7. A pharmaceutical composition useful in the treatment of edema and hypertension which also maintains uric acid at pretreatment levels or causes a decrease which comprises 10 mg. to 500 mg. of a compound of the formula:

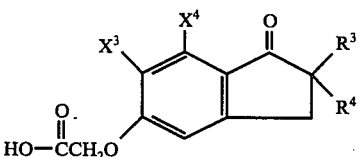

wherein
- R³ and R⁴ are joined together with the carbon atoms to which they are attached to form cycloalkyl containing from 5 to 6 nuclear carbon atoms;
- X³ and X⁴ are the same or different radicals selected from methyl or chloro and the non-toxic pharmacologically acceptable salt derivatives thereof.

8. A pharmaceutical composition useful in the treatment of edema and hypertension which also maintains uric acid level at pretreatment levels or causes a decrease in uric acid levels which comprises 10-500 mg. combined of a compound of the formula:

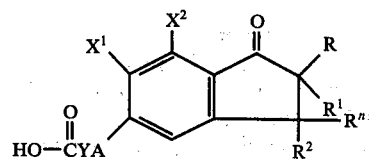

wherein
- A is oxygen or sulfur;
- R and R¹ are joined to form a cycloalkyl or hydroxy cycloalkyl wherein the cycloalkyl radical contains from 3 to 7 carbon atoms; or
- R² is hydrogen, halo, aryl, substituted aryl or lower alkyl;
- R" is methyl or hydrogen;
- X¹ is hydrogen, methyl or halo; and
- X² is methyl or halo; or
- X¹ and X² are joined to form a hydrocarbylene chain containing 3 to 4 carbon atoms; and
- Y is alkylene or haloalkylene containing a maximum of 4 carbon atoms, and the non-toxic, pharmacologically acceptable salt, amide, anhydride and ester derivatives, and an effective anti-hypertensive agent along with a pharmaceutically acceptable carrier.

9. A pharmaceutical composition useful in the treatment of edema and hypertension which also maintains uric acid level at pretreatment levels or causes a decrease in uric acid levels which comprises 10-500 mg. of the formula:

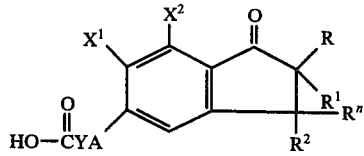

wherein
- A is oxygen or sulfur;
- R and R¹ are joined to form a cycloalkyl, or hydroxy cycloalkyl wherein the cycloalkyl radical contains from 3 to 7 carbon atoms; or
- R² is hydrogen, halo, aryl, substituted aryl or lower alkyl;
- R" is methyl or hydrogen;
- X¹ is hydrogen, methyl or halo; and
- X² is methyl or halo; or
- X¹ and X² are joined to form a hydrocarbylene chain containing 3 to 4 carbon atoms and
- Y is alkylene or haloalkylene containing a maximum of 4 carbon atoms, and the non-toxic, pharmacologically acceptable salt, amide, anhydride and ester derivatives along with a pharmaceutical carrier with the proviso that no two compounds can be exactly the same.

10. A method for the treatment of edema, hyperuricemia and hypertension which comprises administering a unitary dosage of from 10 mg. to 500 mg. of a compound of the formula:

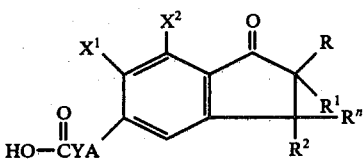

wherein
A is oxygen or sulfur;
R and $R^1$ are joined to form a cycloalkyl or hydroxy cycloalkyl wherein the cycloalkyl radical contains from 3 to 7 carbon atoms; or
$R^2$ is hydrogen, halo, aryl, substituted aryl;
$R''$ is hydrogen or methyl;
$X^1$ is hydrogen, methyl or halo and
$X^2$ is methyl or halo or
$X^1$ and $X^2$ are joined to form a hydrocarbylene chain containing 3 to 4 carbon atoms; and
Y is alkylene or haloalkylene containing a maximum of 4 carbon atoms, and the non-toxic, pharmacologically acceptable salt, amide, anhydride and ester derivatives
in a total daily dose of from 10 mg. to 2000 mg.

11. A method of treatment of edema, hyperuricemia and hypertension which comprises administering a unitary dosage of from 10 mg. to 500 mg. of a compound of the formula:

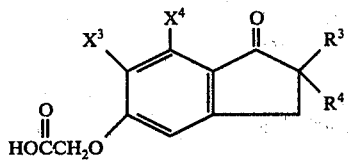

$R^3$ and $R^4$ are joined together with the carbon atoms to which they are attached to form cycloalkyl containing from 5 to 6 nuclear carbon atoms;
$X^3$ and $X^4$ are the same or different radicals selected from methyl or chloro and the non-toxic pharmacologically acceptable salt derivatives thereof
in a total daily dose of from 10 mg. to 2000 mg.

12. A method of treatment according to claim 11 wherein the compound to be administered is one wherein $R^3$ and $R^4$ form cyclopentyl and $X^3$ and $X^4$ are chloro; which is [1'-oxo-6',7'-dichlorospiro(cyclopentane-1,2'-indan)-5'-yloxy]acetic acid.

13. A method of treatment according to claim 11 wherein the compound to be adminstered is one wherein $R^3$ and $R^4$ form cyclohexyl and $X^3$ and $X^4$ are chloro; which is [1'-oxo-6',7'-dichlorospiro(cyclohexane-1,2'-indan)-5'-yloxy]acetic acid.

* * * * *